United States Patent
Even-Chen et al.

(10) Patent No.: US 10,779,746 B2
(45) Date of Patent: Sep. 22, 2020

(54) TASK-OUTCOME ERROR SIGNALS AND THEIR USE IN BRAIN-MACHINE INTERFACES

(71) Applicant: The Board of Trustees of the Leland Stanford Junior University, Palo Alto, CA (US)

(72) Inventors: Nir Even-Chen, Palo Alto, CA (US); Krishna V. Shenoy, Palo Alto, CA (US); Jonathan C. Kao, Los Angeles, CA (US); Sergey Stavisky, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 108 days.

(21) Appl. No.: 15/234,844

(22) Filed: Aug. 11, 2016

(65) Prior Publication Data
US 2017/0042440 A1 Feb. 16, 2017

Related U.S. Application Data

(60) Provisional application No. 62/204,540, filed on Aug. 13, 2015.

(51) Int. Cl.
| | | |
|---|---|---|
| A61B 5/0484 | (2006.01) | |
| A61B 5/0482 | (2006.01) | |
| A61B 5/04 | (2006.01) | |
| A61B 5/00 | (2006.01) | |

(Continued)

(52) U.S. Cl.
CPC ........ *A61B 5/0482* (2013.01); *A61B 5/04012* (2013.01); *A61B 5/7267* (2013.01); *G06N 20/00* (2019.01); *G06N 20/20* (2019.01); *A61B 2503/40* (2013.01); *A61B 2503/42* (2013.01)

(58) Field of Classification Search
None
See application file for complete search history.

(56) References Cited

U.S. PATENT DOCUMENTS

| | | | |
|---|---|---|---|
| 10,223,634 B2 | 3/2019 | Sussillo et al. | |
| 2003/0105409 A1* | 6/2003 | Donoghue | A61B 5/04001 600/545 |

(Continued)

OTHER PUBLICATIONS

Ferrez et al. Simultaneous Real-Time Detection of Motor Imagery and Error-Related Potentials for Improved BCI Accuracy. In proceedings of the 4th Intl. Brain-Computer Interface Workshop and Training Course (2008).*

(Continued)

*Primary Examiner* — Etsub D Berhanu
(74) *Attorney, Agent, or Firm* — KPPB LLP

(57) ABSTRACT

A brain machine interface (BMI) for improving a performance of a subject is provided. The BMI has two decoders that act in real-time and in parallel to each other. The first decoder is for intention execution of a subject's intention. The second decoder is for error detection in a closed-loop error fashion with the first detector and to improve the performance of the first detector. Embodiments of this invention may enable an entirely new way to substantially increase the performance and robustness, user experience, and ultimately the clinical viability of BMI systems.

11 Claims, 11 Drawing Sheets

(51) Int. Cl.
G06N 20/00 (2019.01)
G06N 20/20 (2019.01)

(56) References Cited

U.S. PATENT DOCUMENTS

| | | | |
|---|---|---|---|
| 2004/0073414 A1* | 4/2004 | Bienenstock | G06F 3/015 703/2 |
| 2004/0267320 A1 | 12/2004 | Taylor et al. | |
| 2005/0017870 A1* | 1/2005 | Allison | G06F 3/015 340/4.13 |
| 2005/0228515 A1* | 10/2005 | Musallam | A61F 2/68 700/83 |
| 2010/0274746 A1 | 10/2010 | Rickert et al. | |
| 2010/0280403 A1* | 11/2010 | Erdogmus | A61B 5/0484 600/545 |
| 2011/0092842 A1* | 4/2011 | Decaria | A61B 5/04001 600/544 |
| 2011/0224572 A1 | 9/2011 | Gilja et al. | |
| 2011/0307079 A1* | 12/2011 | Oweiss | A61B 5/048 623/27 |
| 2012/0030696 A1* | 2/2012 | Smith | G06Q 30/02 725/10 |
| 2012/0130266 A1* | 5/2012 | Mathan | A61B 5/4088 600/544 |
| 2013/0311412 A1 | 11/2013 | Lazar et al. | |
| 2014/0194720 A1* | 7/2014 | Hua | A61B 5/6865 600/378 |
| 2015/0269336 A1* | 9/2015 | Duan | A61B 5/0478 702/189 |
| 2016/0048753 A1 | 2/2016 | Sussillo et al. | |
| 2019/0025917 A1* | 1/2019 | Francis | G06F 3/015 |
| 2019/0205731 A1 | 7/2019 | Sussillo et al. | |
| 2019/0333505 A1 | 10/2019 | Stavisky et al. | |

OTHER PUBLICATIONS

Schmidt et al. Online detection of error-related potentials boosts the performance of mental typewriters. BMC Neurosci. 13:19 (2012).*
Artusi et al. Performance of a Simulated Adaptive BCI Based on Experimental Classification of Movement-Related and Error Potentials. IEEE Journal on Emerging and Selected Topics in Circuits and Systems, vol. 1, No. 4, Dec. 2011.*
Spuler et al. Error-related potentials during continuous feedback: using EEG to detect errors of different type and severity. Frontiers in Human Neuroscience, vol. 9, Article 155 (2015).*
Chavarriaga et al. Errare machinale est: the use of error-related potentials in brain-machine interfaces. Frontiers in Neuroscience, vol. 8, Article 208 (2014).*
Subasi et al. EEG signal classification using PCA, ICA, LDA and support vector machines. Expert Systems with Applications 37 (2010) 8659-8666. (Year: 2010).*
Hill et al. Recording Human Electrocorticographic (ECoG) Signals for Neuroscientific Research and Real-time Functional Cortical Mapping. Journal of Visualized Experiments (2012). (Year: 2012).*
Llera. Adaptive Classification on Brain-Computer Interfaces Using Reinforcement Signals. Neural Computation, Jul. 2012. (Year: 2012).*
Shenoy et al., "Combining Decoder Design and Neural Adaptation in Brain-Machine Interfaces", Neuron, vol. 84, No. 4, Nov. 19, 2014, 16 pgs.
Shenoy et al., "Cortical Control of Arm Movements: A Dynamical Systems Perspective", Annual Rev Neuroscience, vol. 36, Jul. 8, 2013, E-Publication May 29, 2013, 26 pgs.
Simonyan et al., "New Developments in Understanding the Complexity of Human Speech Production", The Journal of Neuroscience, vol. 36, No. 45, Nov. 9, 2016, pp. 11440-11448.
Stavisky et al., "A High Performing Brain-Machine Interface Driven by Low-Frequency Local Field Potentials Alone and Together with Spikes", HHS Public Access—Author Manuscript, 36 pgs., published in final form as Journal of Neural Engineering, vol. 12, No. 3, Jun. 2015.
Stavisky et al., "Decoding Speech from Intracortical Multielectrode Arrays in Dorsal "Arm/Hand Areas" of Human Motor Cortex", Annual Conference of the IEEE Engineering in Medicine and Biology Society, Jul. 2018, 5 pgs.
Suppes et al., "Brain Wave Recognition of Words", Proceedings of the National Academy of Sciences, vol. 94, No. 26, Dec. 23, 1997, 5 pgs.
Sussillo et al., "A recurrent neural network for closed-loop intracortical brain-machine interface decoders", Journal of neural engineering 9.2: 026027 Published Mar. 19, 2012, 10 pgs.
Sussillo et al., "Making brain-machine interfaces robust to future neural variability", Nature Communications, Published Dec. 13, 2016, 12 pgs.
Sutskever et al., "Generating Text with Recurrent Neural Networks", Proceedings of the 28th International Conference on Machine Learning (ICML-11). 2011, 8 pgs.
Tankus et al., "Structured Neuronal Encoding and Decoding of Human Speech Features", HHS Public Access—Author Manuscript, 11 pgs., published in final form as Nature Communications, vol. 3, 2012.
Towle et al., "ECoG Gamma Activity During a Language Task: Differentiating Expressive and Receptive Speech Areas", Brain, vol. 131, No. 8, Aug. 2008, pp. 2013-2027.
Trautmann et al., "Accurate Estimation of Neural Population Dynamics Without Spike Sorting", bioRxiv, Dec. 5, 2017, 42 pgs.
Vainio et al., "Shared Processing of Planning Articulatory Gestures and Grasping", Experimental Brain Research, vol. 232, No. 7, Jul. 2014, pp. 2359-2368.
Waldert et al., "Influence of Spiking Activity on Cortical Local Field Potentials", The Journal of Physiology, vol. 21, Nov. 1, 2013, E Publication Aug. 27, 2013, pp. 5291-5303.
Willett et al., "Improving Brain-Machine Interface Performing by Decoding Intended Future Movements", NIH Public Access—Author Manuscript, 27 pgs., published in final form as J. Neural Engineering, vol. 10, No. 2, Apr. 2013, E-Publication Feb. 21, 2013.
Wise et al., "Premotor and Parietal Cortex: Corticocortical Connectivity and Combinatorial Computations", Annu Rev Neuroscience, vol. 20, 1997, pp. 25-42.
Yang et al., "Sensorimotor Experience and Verb-Category Mapping in Human Sensory, Motor and Parietal Neurons", HHS Public Access—Author Manuscript, 29 pgs., published in final form as Cortex, vol. 92, Jul. 2017, pp. 304-319.
Ferrez et al., "EEG-Based Brain-Computer Interaction: Improved Accuracy by Automatic Single-Trial Error Detection", Advances in Neural Information Processing Systems 20, 2007, 8 pgs.
Andersen et al., "Selecting the Signals for a Brain-Machine Interface", Current Opinion in Neurobiology, vol. 14, No. 6, Dec. 2004, pp. 720-726.
Anumanchipalli et al., "Intelligible Speech Synthesis from Neural Decoding of Spoken Sentences", bioRxiv, Nov. 29, 2018, 32 pgs.
Bacher et al., "Neural Point-and-Click Communication by a Person Wth Incomplete Locked-In Syndrome", Neurorehabilitation and Neural Repair, vol. 29, No. 5, Nov. 10, 2014, pp. 462-471.
Bouchard et al., "Control of Spoken Vowel Acoustics and the Influence of Phonetic Context in Human Speech Sensorimotor Cortex", The Journal of Neuroscience, vol. 34, No. 38, Sep. 17, 2014, pp. 12662-12677.
Bouchard et al., "Functional Organization of Human Sensorimotor Cortex for Speech Articulation", HHS Public Access—Author Manuscript, 21 pgs., published in final form as Nature, vol. 495, No. 7441, Mar. 21, 2013, pp. 327-332.
Bouchard et al., "Neural Decoding of Spoken Vowels from Human Sensory-Motor Cortex with High-Density Electrocorticography", 36th Annual International Conference of the IEEE Engineering in Medicine and Biology Society, Aug. 26-30, 2014, Chicago, IL, 4 pgs.
Breshears et al., "A Probabilistic Map of the Human Ventral Sensorimotor Cortex Using Electrical Stimulation", Journal of Neurosurgery, vol. 123, No. 2, Aug. 2015, E Publication May 15, 2015, 10 pgs.

(56) References Cited

OTHER PUBLICATIONS

Brumberg et al., "Classification of Intended Phoneme Production from Chronic Intracortical Microelectrode Recordings in Speech-Motor Cortex", Frontiers in Neuroscience, vol. 5, May 12, 2011, 12 pgs.

Chakrabarti et al., "Progress in Speech Decoding from the Electrocorticogram", Biomedical Engineering Letters, vol. 5, No. 1, Mar. 2015, pp. 10-21.

Chan et al., "Decoding Word and Category-Specific Spatiotemporal Representations from MEG and EEG", NIH Public Access—Author Manuscript, 24 pgs., published in final form as Neuroimage, vol. 54, No. 4, Feb. 14, 2011, pp. 3028-3039.

Chan et al., "Speech-Specific Tuning of Neurons in Human Superior Temporal Gyrus", Cerebral Cortex, vol. 24, No. 10, Oct. 2014, pp. 2679-2693.

Chestek et al., "Long-term stability of neural prosthetic control signals from silicon cortical arrays in rhesus macaque motor cortex", Journal of neural engineering, 8(4):045005, Jul. 2011, 11 pgs.

Cheung et al., "The Auditory Representation of Speech Sounds in Human Motor Cortex", eLife, Mar. 4, 2016, 19 pgs.

Churchland et al., "Techniques for Extracting Single-Trial Activity Patterns from Large-Scale Neural Recordings", NIH Public Access—Author Manuscript, 16 pgs., published in final form as Current Opinion in Neurobiology, vol. 17, No. 5, Oct. 2007, pp. 609-618.

Collinger et al., "7 degree-of-freedom neuroprosthetic control by an individual with tetraplegia", NIH Public Access—Author Manuscript, 17 pgs., published in final form as "High-Performance Neuroprosthetic Control by an Individual with Tetraplegia", The Lancet, vol. 381, No. 9866, Feb. 16, 2013, 17 pgs.

Creutzfeldt et al., "Neuronal Activity in the Human Lateral Temporal Lobe: I. Responses to Speech", Experimental Brain Research, vol. 77, No. 3, 1989, pp. 451-475.

Cunningham et al., "A closed-loop human simulator for investigating the role of feedback control in brain-machine interfaces", Journal of neurophysiology, 105(4):1932-1949, Apr. 2011.

Daffau et al., "The Role of Dominant Premotor Cortex in Language: A Study Using Intraoperative Functional Mapping in Awake Patients", Neuroimage, vol. 20, No. 4, Dec. 2003, pp. 1903-1914.

Einevoll et al., "Modelling and Analysis of Local Field Potentials for Studying the Function of Cortical Circuits", Nature Review Neuroscience, vol. 14, No. 11, Nov. 2013, pp. 770-785.

Even-Chen et al., "Auto-Deleting Brain Machine Interface: Error Detection Using Spiking Neural Activity in the Motor Cortex", 37th Annual International Conference of the IEEE Engineering in Medicine and Biology Society, Aug. 25-29, 2015, Milan, Italy, 5 pgs.

Even-Chen et al., "Feasibility of Automatic Error Detect-and-Undo System in Human Intracortical Brain—Computer Interfaces", IEEE Transactions on Biomedical Engineering, vol. 65, No. 8, Aug. 2018, pp. 1771-1784.

Fan et al., "Intention Estimation in Brain-Machine Interfaces", NIH Public Access—Author Manuscript, 28 pgs., published in final form as Journal Neural Engineering, vol. 11, No. 1, Feb. 2014.

Gilja et al., "A High-Performance Neural Prosthesis Enabled by Control Algorithm Design", Nature Neuroscience, vol. 15, No. 12, Dec. 2012, Published Online: Nov. 18, 2012, pp. 1752-1757.

Golub et al., "Internal Models Engaged by Brain-Computer Interface Control", NIH Public Access—Author Manuscript, 11 pgs., published in final form as 34th Annual International Conference of the IEEE EMBS, vol. 2012, 2012, pp. 1327-1330.

Guenther et al., "A Wireless Brain-Machine Interface for Real-Time Speech Synthesis", PLoS One, vol. 4, No. 12, Dec. 9, 2009, 11 pgs.

Herff et al., "Automatic Speech Recognition from Neural Signals: A Focused Review", Front Neuroscience, vol. 10, No. 429, Sep. 2016, pp. 1-7.

Herff et al., "Brain-to-text: decoding spoken phrases from phone representations in the brain", Frontiers in Neuroscience, vol. 9, No. 217, Jun. 12, 2015, 11 pgs.

Hochberg et al., "Neuronal ensemble control of prosthetic devices by a human with tetraplegia", Nature, vol. 442, No. 7099, Jul. 13, 2006, pp. 164-171.

Homer et al., "Sensors and Decoding for Intracortical Brain Computer Interfaces", Annual Review of Biomedical Engineering, vol. 15, Jul. 2013, 25 pgs.

Jozefowicz et al., "Exploring the Limits of Language Modeling", arXiv:1602.02410v2, Feb. 11, 2016, 11 pgs.

Kao et al., "Information Systems Opportunities in Brain-Machine Interface Decoders", Proceedings of the IEEE, vol. 102, No. 5, May 2014, 17 pgs.

Kellis et al., "Decoding Spoken Words Using Local Field Potentials Recorded from the Cortical Surface", NIH Public Access—Author Manuscript, 20 pgs., published in final form as Journal of Neural Engineering, vol. 7, No. 5, Oct. 2010.

Kim et al., "Neural control of computer cursor velocity by decoding motor cortical spiking activity in humans with tetraplegia", Journal of neural engineering, 5(4):455-476, Dec. 2008.

Leuthardt et al., "Using the Electrocorticographic Speech Network to Control a Brain-Computer Interface in Humans", NIH Public Access—Author Manuscript, 22 pgs., published in final form as Journal of Neural Engineering, vol. 8, No. 3, Jun. 2011.

Lotte et al., "Electrocorticographic Representations of Segmental Features in Continuous Speech", Frontiers in Human Neuroscience, vol. 9, Feb. 24, 2015, 13 pgs.

Malik et al., "Efficient Decoding with Stead-State Kalman Filter in Neural Interface Systems", NIH Public Access—Author Manuscript, 25 pgs., published in final form as IEEE Trans Neural System Rehabilitation Engineering, vol. 19, No. 1, Feb. 2011, pp. 25-34.

Martin et al., "Decoding Spectrotemporal Features of Overt and Covert Speech from the Human Cortex", Front Neuroengineering, vol. 7, May 27, 2014, 15 pgs.

Meister et al., "Motor Cortex Hand Area and Speech: Implications for the Development of Language", Neuopsychologia, vol. 41, No. 4, 2003, pp. 401-406.

Mugler et al., "Direct Classification of all American English Phonemes Using Signals from Functional Speech Motor Cortex", NIH Public Access—Author Manuscript, 16 pgs., published in final form as Journal of Neural Engineering, vol. 11, No. 3, Jun. 2014.

Mulliken et al., "Decoding Trajectories from Posterior Parietal Cortex Ensembles", Journal of Neuroscience, vol. 28, No. 48, Nov. 26, 2008, pp. 12913-12926.

Nguyen et al., "Inferring Imagined Speech using EEG Signals: A New Approach Using Riemannian Manifold Features", Journal of Neural Engineering, vol. 15, No. 1, 2017, 16 pgs.

Nuyujukian et al., "A High-Performance Keyboard Neural Prosthesis Enabled by Task Optimization", IEEE Transactions on Biomedical Engineering, vol. 62, No. 1, Sep. 4, 2014, 9 pgs.

Nuyujukian et al., "Monkey Models for Brain-Machine Interfaces: The Need for Maintaining Diversity", 33rd Annual International Conference of the IEEE EMBS, Aug. 30-Sep. 3, 2011, Boston, Massachusetts, 5 pgs.

Orsborn et al., "Closed-Loop Decoder Adaptation Shapes Neural Plasticity for Skillful Neuroprosthetic Control", Neuron, vol. 82, No. 6, Jun. 2014, pp. 1380-1393.

Pandarinath et al., "High performance communication by people with paralysis using an intracortical brain-computer interface", Elife, vol. 6, Feb. 21, 2017, 27 pgs.

Ramsey et al., "Decoding Spoken Phonemes from Sensorimotor Cortex with High-Density ECoG Grids", Neuroimage, Oct. 15, 2018, E Publication Oct. 7, 2017, 11 pgs.

Ryu et al., "Human cortical prostheses: lost in translation?", Neurosurgical Focus, 2009, 11 pgs.

Sahin et al., "Sequential Processing of Lexical, Grammatical, and Phonological Information within Broca's Area", NIH Public Access—Author Manuscript, 11 pgs., published in final form as Science, vol. 326, No. 5951, Oct. 16, 2009, pp. 445-449.

Santhanam et al., "A high-performance brain—computer interface", Nature, vol. 442, No. 7099, Jul. 13, 2006, pp. 195-198.

Shadmehr et al., "Error Correction, Sensory Prediction, and Adaptation in Motor Control", Annu Rev Neuroscience, vol. 33, Jan. 2010, pp. 89-108.

\* cited by examiner

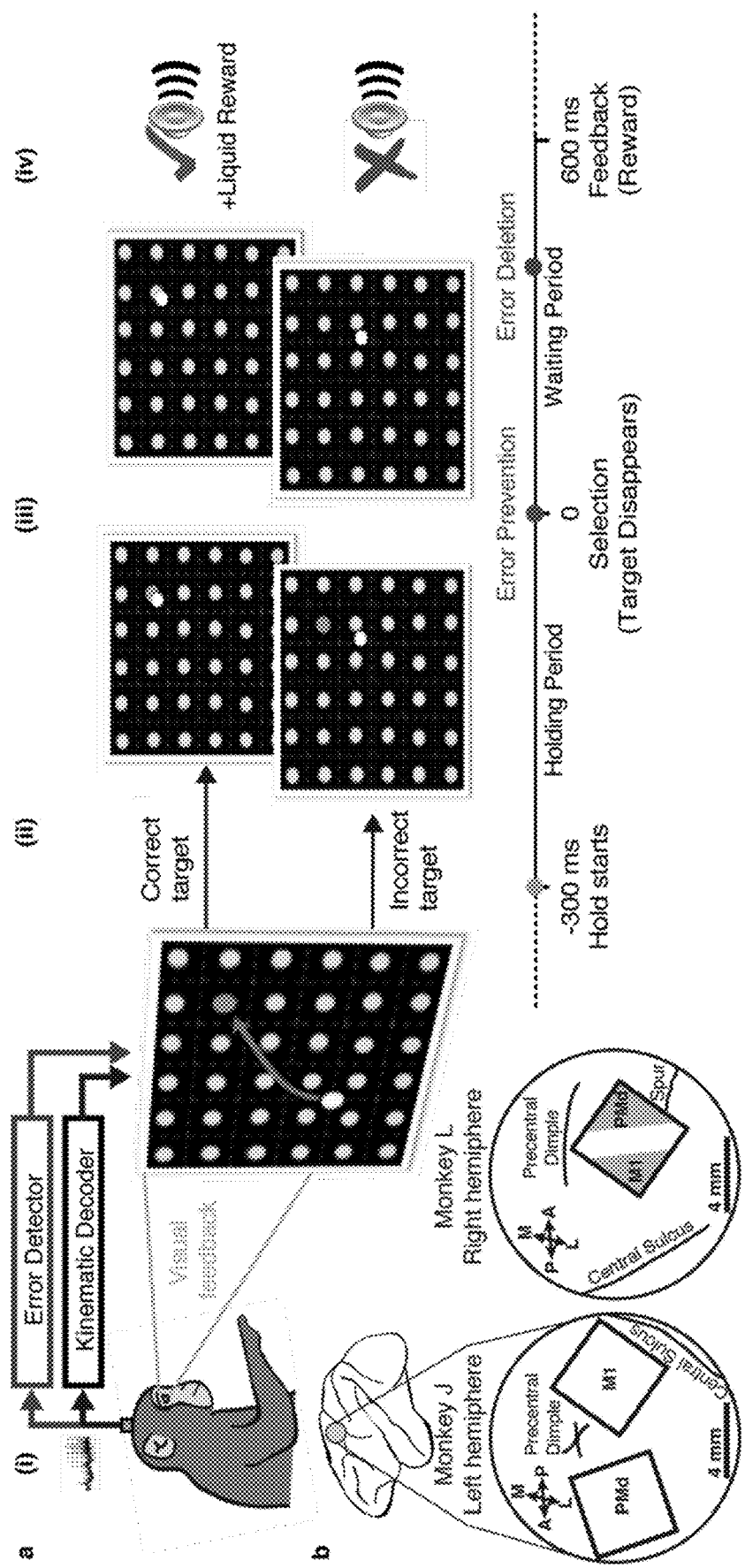

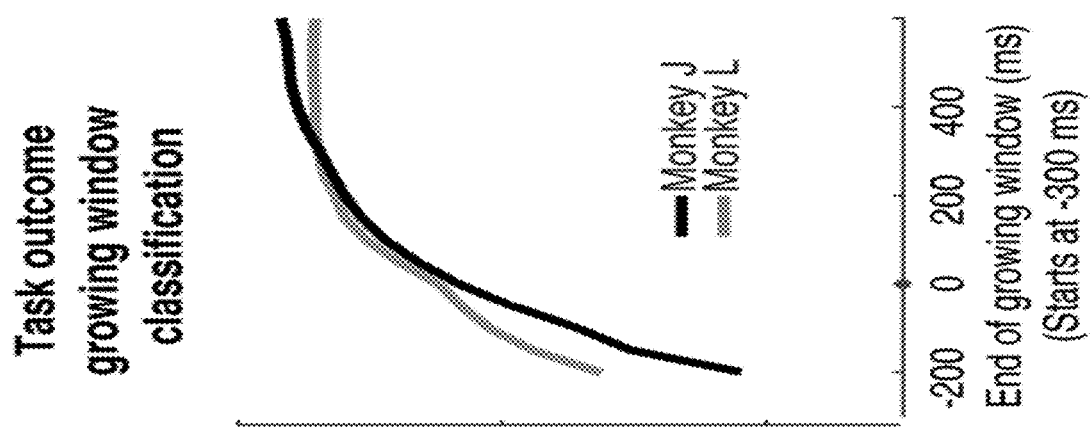
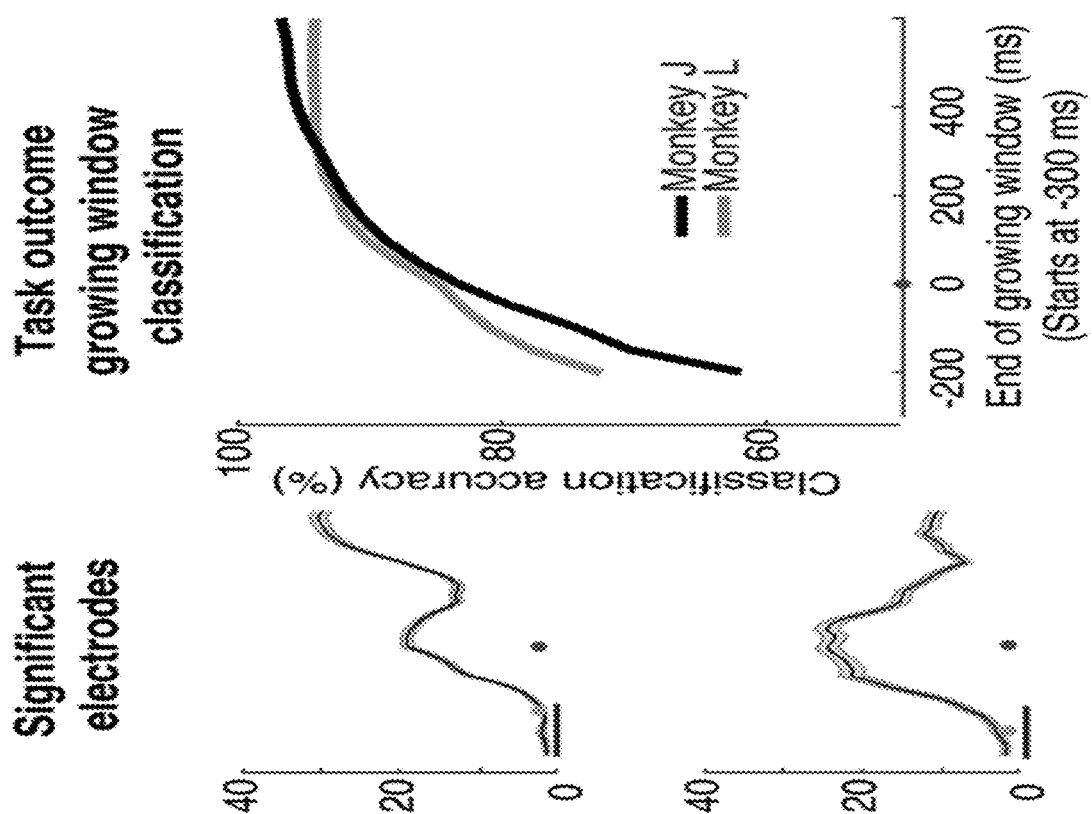
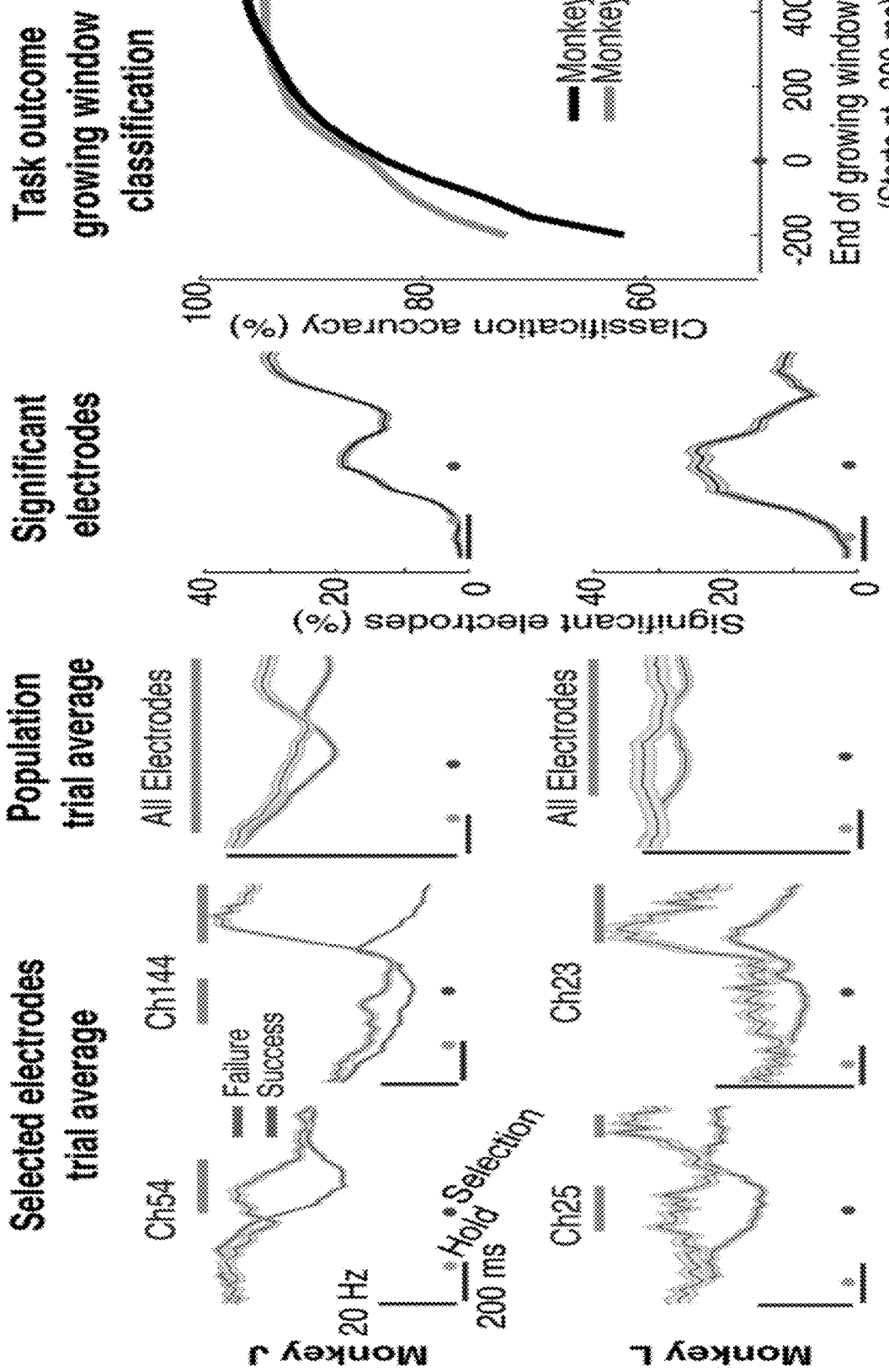

Online BMI error-detector time windows

Online 'Typing Rate' comparison

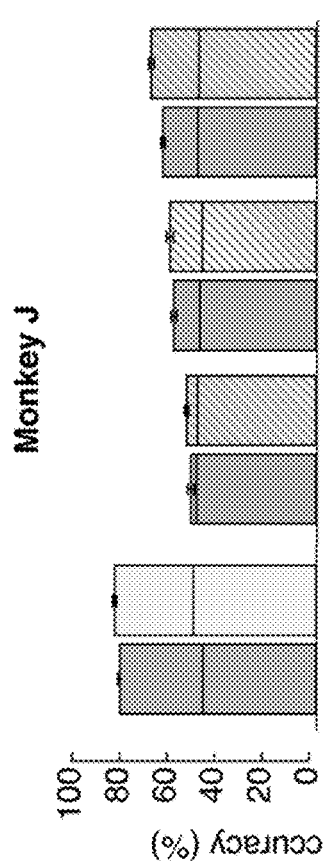
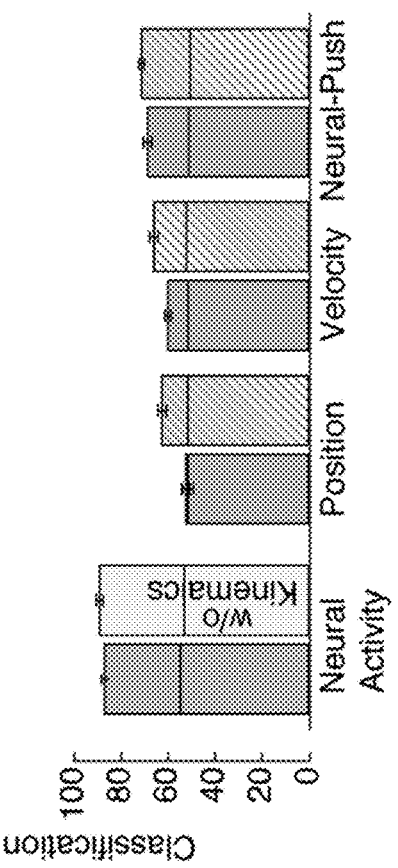
FIG. 7A Kinematic control analysis
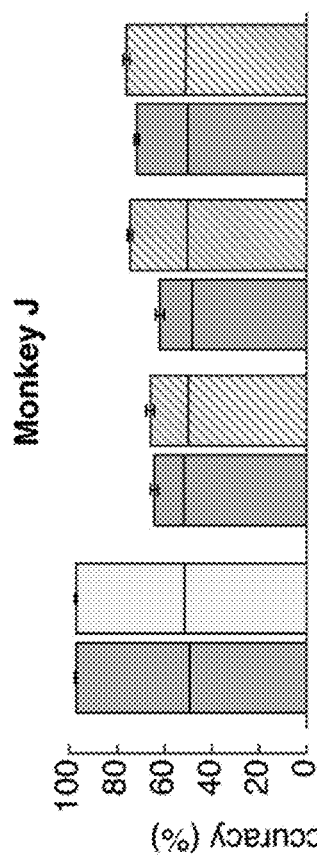
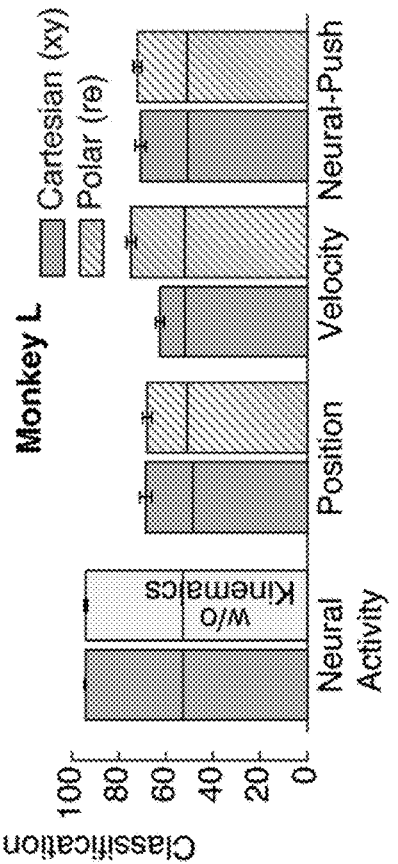
FIG. 7B

FIG. 9A
Explained variance
FIG. 9B
Rotated PCs Vs. Time
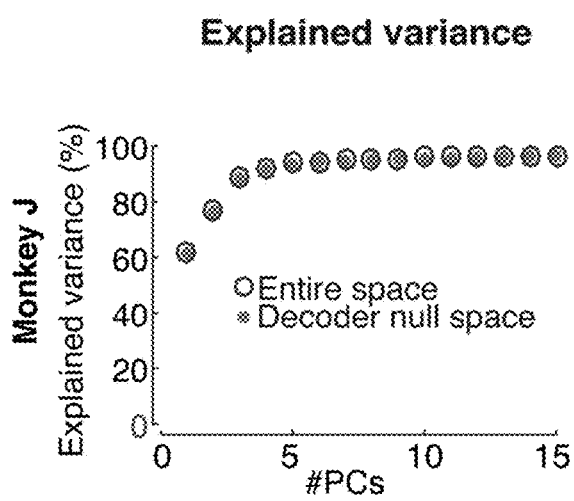
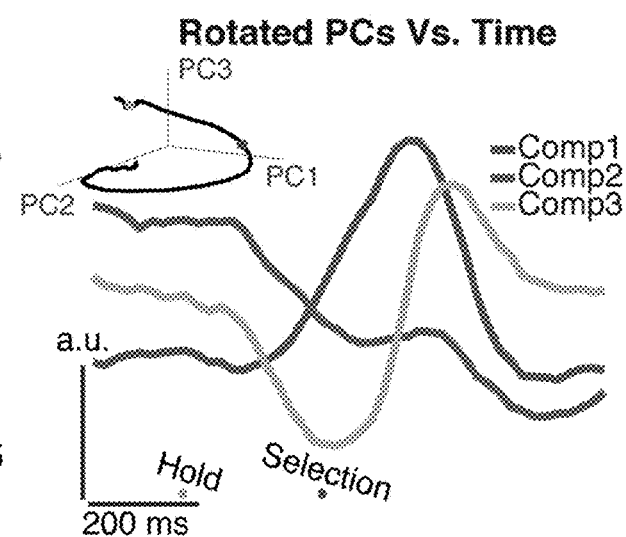
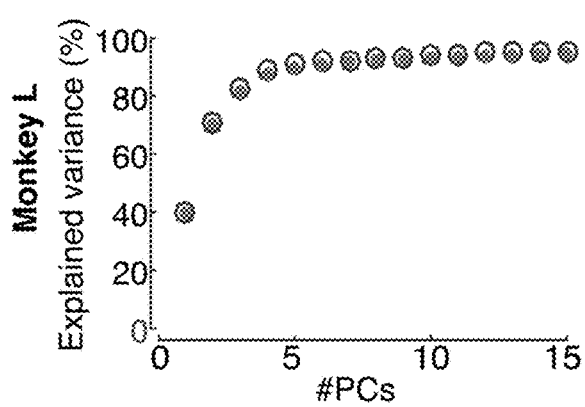
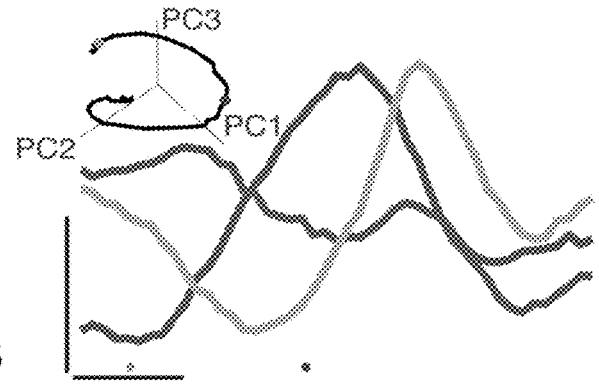

US 10,779,746 B2

TASK-OUTCOME ERROR SIGNALS AND THEIR USE IN BRAIN-MACHINE INTERFACES

CROSS-REFERENCE TO RELATED APPLICATIONS

This application claims priority from U.S. Provisional Patent Application 62/204,540 filed Aug. 13, 2015, which is incorporated herein by reference.

STATEMENT OF GOVERNMENT SPONSORED SUPPORT

This invention was made with Government support under contract HD075623 awarded by the National Institutes of Health, and under contract N66001-10-C-2010 awarded by the Defense Advanced Research Projects Agency. The Government has certain rights in the invention.

FIELD OF THE INVENTION

This invention relates to brain machine interfaces.

BACKGROUND OF THE INVENTION

Systems with the ability to monitor their performance and identify mistakes unlock the capability to adapt in response to errors and better achieve their desired goals. There is no better example of this principle than the nervous system, which makes widespread use of feedback both to correct errors shortly after they occur and to adapt to minimize future errors.

During the control of movement, error signals are used to correct perturbations and update the brain's internal model. The same principle is also of clear utility to engineered systems and underlies control systems.

Brain-machine interfaces (BMIs), which are being developed to restore movement to people with paralysis, would benefit from an outcome error detection when they performed the wrong action. The present invention advances the art in providing technology in which outcome error detection can be used in BMIs.

SUMMARY OF THE INVENTION

The present invention provides a brain machine interface (BMI) for improving a performance of a subject. The BMI has two decoders that act in real-time and in parallel to each other. The first decoder is for intention execution of a subject's intention. The first decoder is capable of: (i) acquiring brain activity from a brain area of the subject and (ii) executing the subject's intention by decoding the acquired brain activity from the brain area. The second decoder is for error detection in a closed-loop error fashion with the first detector and to improve the performance of the first detector. The second decoder is capable of: (j) acquiring brain activity from a different or the same brain area of the subject and (jj) translating the acquired brain activity from the brain area in an error signal of the performance of the subject, which is then used to improve performance. The second decoder could have an error-prevention mode or an error auto-deletion mode and in one embodiment is a learnt classifier. The subject's intention could be the subject's intension for movement. In one example, the brain area is the motor cortex.

In a typical BMI control setting, a subject corrects his/her mistakes manually, for example by selecting the 'delete' key in a typing task. This manual corrective action is time-consuming. Using the BMI control according to this invention, the error detector will automatic detect or prevent errors and spare the user from manual correction. Application of such BMI would improve the BMI performance. Such BMI with error detection (e.g. prevention and auto-deletion) techniques could be applied to a broad range of BMI tasks to intervene with corrective actions. In a computer cursor control task, it can be used to prevent incorrect clicks during typing. During control of a robotic arm, task outcome error detection can likely be used to cancel the last command (e.g., grasping) and return to a previous state (e.g., the state of the robotic arm a second ago). In addition, error signals can also be used to update the decoder parameters and prevent future errors. While execution error can be used to update decoder parameters themselves, outcome error can be used to adjust the learning rate of an adaptive algorithm, by, for example, increasing the learning rate after errors. As such, embodiments of this invention may enable an entirely new way to substantially increase the performance and robustness, user experience, and ultimately the clinical viability of BMI systems.

BRIEF DESCRIPTION OF THE DRAWINGS

FIGS. 1A-B show according to an exemplary embodiment of the invention an experimental layout and task timeline. In FIG. 1A a monkey performs a BMI grid task by controlling the cursor using a velocity Kalman filter (black pathway). (i) Monkey's goal is to move the cursor ('white' disk at bottom of arrow) to the cued 'green' target (at the arrow end of the arrow) among the potential 'yellow' targets (dots on the screen). The target selection areas were non-overlapping and collectively spanned a 24×24 $cm^2$ workspace. Therefore, within the grid workspace, the cursor was always in the acquisition window (whose height and width was 24/n cm, n=6-8) of a possible target. Since he observes the screen, he nominally identifies task errors (green feedback path). We built an error detector (red path) that was integrated into the BMI to perform closed-loop error prevention or error auto-deletion (red pathway) before ('Error Prevention') and during ('Error Correction') the waiting period (iii). (ii) Holding the cursor over a target (starts at the 'orange' timeline dot) for 300-400 ms selects that target. When the correct target ('green') is being held, the target's color changes to 'blue'. (iii) After selection ('green' timeline dot), the cued target disappears and (iv) the monkey waits 600 ms for an auditory feedback tone and, in successful trials, a reward. A new trial starts after an additional 400 ms. In FIG. 1B shows microelectrode array location in motor cortex (J and L), as estimated visually from local anatomical landmarks.

FIGS. 2A-D show according to an exemplary embodiment of the invention single trial decoding of trial outcome-dependent neural differences. 'Orange' and 'green' (t=0) dots (now in grey scale) show hold start and target selection time, as in FIG. 1A ('orange' dot, now in grey scale) is the left of the two dots above each x-axis). FIG. 2A shows trial-averaged firing rates (mean±SEM) of selected electrodes during failed (red, which are in grey scale the upper data lines in FIGS. 2A-C)) and successful (blue which are in grey scale the bottom data lines in FIGS. 2A-C)) trials. Gray bars indicate times with significance differences (t-test, $p<0.05$, Bonferroni corrected). FIG. 2B shows population trial averaged firing rates. FIG. 2C shows percentage of electrodes that show significant differences as a function of time (mean±SEM). FIG. 2D shows offline trial outcome decoding accuracy as a function of the end of the growing decoded time window, which starts at 300 ms before selection.

FIG. 3A shows time windows used for error detection, relative to target selection time (t=0). FIG. 3B shows 'typing rate' comparisons between a standard BMI (gray) and a BMI augmented with online error detection. Two modes of error detection were evaluated: error prevention ('green') and error auto-deletion ('purple').

FIG. 4A shows monkey J's neural activity was projected into two PCs with high (above 50%) directional variance (43% and 12% of the variance). Pie charts show relative variance contribution of the average error signal ('black') and the direction of the error ('yellow'). FIG. 4B shows error direction classification accuracy of the four directions using neural data projected into six leading PCs.

FIGS. 7A-B show according to an exemplary embodiment of the invention control experiments examining the influence of kinematics on the decoded trial outcome. Comparison of single-trial outcome decoding accuracy using different data: neural activity ('orange'), neural activity after regressing out kinematics ('w/o Kinematics'), cursor position, cursor velocity and neural-push in Cartesian and Polar coordinate systems. FIG. 7A shows classification using the entire time window of 300 ms before until 600 ms after target selection time. FIG. 7B shows classification using the preselection time window of 300 ms before selection until target selection time.

FIGS. 9A-B show according to an exemplary embodiment of the invention low-dimensional representation of the putative outcome error signal. We performed principal component analysis (PCA) on the difference of condition (success and failure) firing rate averages to extract the neural activity that covaried with outcome. FIG. 9A shows percentage of cumulative explained variance as a function of the number of principal components (PCs) (red) and the variance explained when the PCs were projected into the decoder-null space (gray). (B-inset) 3D visualization of the neural activity (difference between average success and fail trial firing rates) projected into the three leading PCs. "Corkscrew" dynamics are present in both monkeys. FIG. 9B shows time course of the projections into the three leading PCs (rotated to align the "Corkscrew" dynamics).

DETAILED DESCRIPTION

Figure 3A:
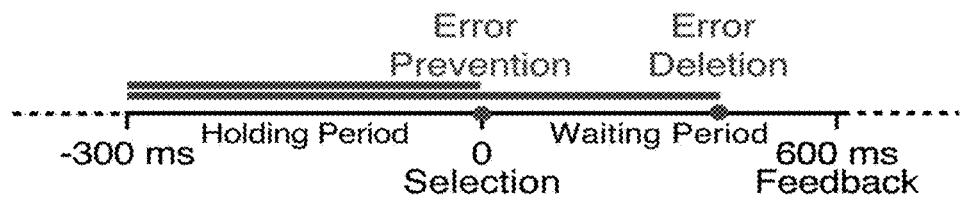
FIGS. 3A-B show according to an exemplary embodiment of the invention online BMI error detector.

In this invention, the question whether an engineered system that directly interfaces with the neural system, i.e. a brain-machine interface (BMI) for translating movement intention into prosthesis output, can exploit the fact that both it and the biological system it is connected to share a common error detection goal.

A variety of error signals, which provide feedback on our actions and the environment, have been investigated in the last few decades and potentially can be used to improve BMI performance. In this invention, we investigated the task-outcome error signal, which arises when the goal of the movement was not achieved. It was previously unknown whether this signal is present in motor cortical regions typically targeted for BMIs. Therefore, in this invention we asked two primary questions:

(1) is an outcome error signal exists in the dorsal premotor (PMd) and primary motor (M1) cortex?
(2) can decoding this signal benefit BMI performance?

BMIs would benefit from an outcome error detection when they performed the wrong action. Current intracortical BMIs decode only neural correlates of movement intention from the cortex, either in pre-clinical animal model experiments or in clinical trial evaluations in people with paralysis. While there has been work in developing adaptive BMI decoders that update their kinematic decoding parameters in response to externally specified errors or inferred errors from the statistics of the system's output, intracortical BMI designs have not explored the utility of a biological task outcome error signal.

A BMI user is typically provided constant visual feedback of the BMI-controlled device (e.g., computer cursor) and of the BMI behavioral goal (such as the target on the screen), and is thus aware of their BMI performance. It has long been appreciated that visual feedback is one of several important sources of sensory feedback that is used to improve natural behavior and BMI-based behavior. It is therefore reasonable to postulate that neural correlates of BMI-based behavioral errors exist somewhere in the brain.

In this invention, we provide an innovative approach of closed-loop error detector in parallel to the traditional BMI decoder. In one embodiment, the decoder detects outcome error signal in real-time, from the same electrodes used to decode kinematics, and intervene with corrective action to improve performance. Intracortical recordings were used to investigate the existence of an outcome error signal in PMd and M1. Specifically, we assessed the ability to detect that a wrong key on a virtual keyboard was selected using a BMI cursor. We report two key findings: first, we found for the first time that putative task-outcome error signals are present in PMd and M1; second, we designed BMI decoder algorithms and measured BMI performance demonstrating that this signal can be employed to increase BMI performance.

Results

We present here the analysis of a putative outcome error signal recorded from PMd and M1 of two monkeys performing a BMI 'typing task'. First, we analyzed single unit and trial-averaged activity across the population, and decoded the task outcome on a single trial basis from neural activity. Second, we present performance improvement of an online BMI error detector which intervene on the user's behalf by preventing or "undoing" incorrect target selections. Third, to further investigate the putative outcome error signal, we conducted control experiments to establish that it could not be explained away as resulting from several potentially confounding task correlates; and we analyzed its low-dimensional neural representation structure to reveal other properties, e.g. its directionality independence. Lastly, we explored the feasibility of using a different neural signal to not only detect that the incorrect target was selected, but to also decode the discrepancy direction to the target.

Behavioral Task

Two rhesus macaques (J and L) were trained to control a BMI cursor using intracortical spike signals recorded from multi-electrode arrays in M1 and PMd (FIG. 1B, see Methods infra—BMI Cursor Control). Neural signals were processed in real time with a mathematical decoder algorithm to generate 2-dimensional BMI cursor velocity control signals.

Our experiment simulated a 'typing task': the monkeys had to acquire a specific correct target cued in green, which was amongst an n×n (n=6-8) keyboard-like grid of selectable yellow targets using a BMI-controlled cursor (FIG. 1A, i). The monkeys 'selected' a target by keeping the BMI cursor within that target's acceptance window for 300 ms (monkey J) or 400 ms (L). When the cursor was within the acceptance window of the correct target, the color of the target changed from green to blue (FIG. 1A, ii). Dwelling over an incorrect target resulted in no color change. Following a target selection, that trial's prompted target reverted to yellow (FIG. 1A, iii), signifying that it was no longer active.

We delayed task-outcome feedback for 600 ms following target selection (FIG. 1A, iv) to temporally separate neural activity reflecting the monkey's (presumed) recognition of the task's outcome from neural activity explicitly related to receiving the feedback (e.g., drinking a liquid reward). Feedback for successful trials included an audio tone and a liquid reward, while failed trials resulted in a different tone and no liquid reward. After an additional 400 ms, a new trial was initiated by prompting a new target in the grid. If no target was selected within the time limit of 5 sec, the trial ended in failure. Only 3% (J) and 9% (L) of the trials were failed this way. These timed out trials were omitted from analyses. When aligning trials across conditions, data were aligned to target selection time (t=0, FIG. 1A, iii, 'green' dot).

We conducted six (J) and four (L) days of closed-loop BMI experiments. Each day we calibrated the task difficulty by changing grid size and hold time to keep the monkey's success rate at ~80% (actual experimental session success rates ranged from 76% to 82%). This difficulty was chosen to balance having a sufficient number of failed trials with which to study neural activity following a failure, against frustrating the monkey or having failure be the expectation rather than the exception.

Task Outcome-Related Neural Differences

First, to investigate whether motor cortical activity reflects task outcome, we compared the trial-averaged activity from successful and failed trials (selected electrodes are presented in FIG. 2A). In both monkeys, we found that there are times before and after target selection when neural activity is different between successful and failed trials (FIG. 2A gray bars, t-test with Bonferroni correction, p<0.05). We also found that the neural activity tends, on average across all electrodes, to have higher firing rates during failed trials when compared to successful trials (FIG. 2B gray bars, t-test with Bonferroni correction, p<0.05). Second, to evaluate to what extent this task outcome difference was observed across the entire recorded population, we computed the percentage of units that showed significant firing rate differences between successful and failed trials (t-test, p<0.05 with Bonferroni correction) as a function of time using trial bootstrap (FIG. 2C, see Methods infra). We found that the activity of more than 18±1% (J) and 25±1% (L) of units were modulated by task outcome around target selection time. Further, we found that at least 10% of units were modulated for task outcome 155±10 ms (J) and 161±13 ms (L) (mean±std) after the hold period starts. Additionally, we found that PMd reflected task outcome earlier than M1. Specifically, in PMd at least 10% of the population was modulated by task outcome 117±10 ms (J) and 80±20 ms (L) earlier than in M1 (t-test, p<0.01). From these results, we can infer that the activity of many neurons in motor cortex is correlated with task outcome. We show below, through various controls, that this putative outcome error signal is not merely a result of indirect outcome correlates, such as movement. However, we first focus on whether this putative outcome error signal can be beneficially incorporated to improve BMIs.

Single Trial Outcome Decoding

Figure 5:
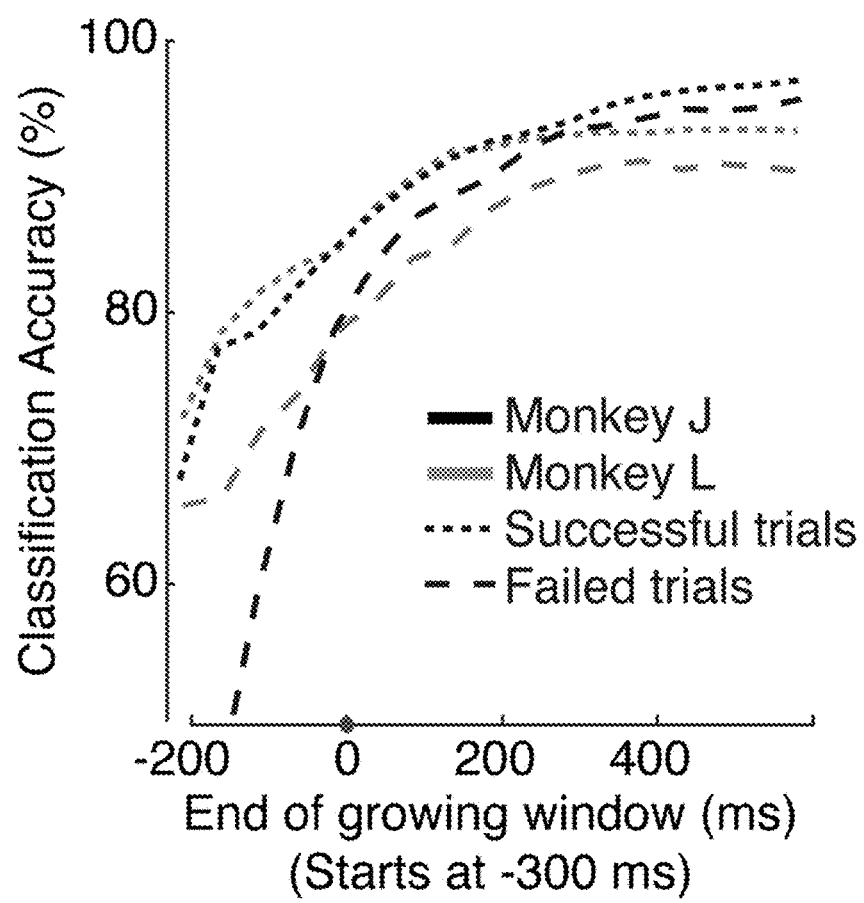
FIG. 5 shows according to an exemplary embodiment of the invention offline trial outcome decoding accuracy by condition (success/failure) as a function of the end of decoded time window. Time points correspond to the end of a growing time window which begins 300 ms before target selection. Sensitivity ('Successful trials', true positive rate) and specificity ('Failed trials', true negative rate) as function of time, i.e. the accuracy of detecting successful trials and detecting failed trials. Before target selection, the decoding accuracy for failed trials is low compared to successful trials. However, over time the gap in decode accuracy decreases and is less than 6% different at selection time. One interpretation of the diminishing decoding accuracy differences is related to the monkey's confidence in the expected outcome. That is, while in successful trials he is relatively confident in his success during the hold period, in failed trials, he still has time to correct and his confidence in the outcome is low.

To better understand when during a trial information signaling the trial's outcome was present, and to explore the potential use of our findings for BMI error detection, we analyzed the trial-outcome decoding accuracy as a function of time. We decoded trial outcome based solely on neural activity in growing time windows using principal components analysis (PCA) and linear support vector machine (SVM) (see Methods). The time windows start from 300 ms before target selection and end between 200 ms before until 600 ms after target selection (FIG. 2D). Trial outcome decoding accuracy increased with time and converged to 97±0.5% (J) and 94±1% (L) around 400 ms after target selection, similar to the saturation times found in ECoG offline error detection. In addition, we found that decoding accuracy at selection time (t=0 ms) was substantially above chance at 83±1% (J) and 85±2% for (L). We also verified that our decoder is not biased towards one outcome (e.g., always predicting success), we computed the sensitivity (true positive rate) and specificity (true negative rate) values as function of time, i.e. the accuracy of detecting successful trials and detecting failed trials FIG. 5). This high offline decoding accuracy encouraged us to implement an online error detector in a BMI that automatically detects errors, and prevents or corrects them.

Online BMI's Error Prevention and Auto-Deletion Improve Performance

Figure 3B:
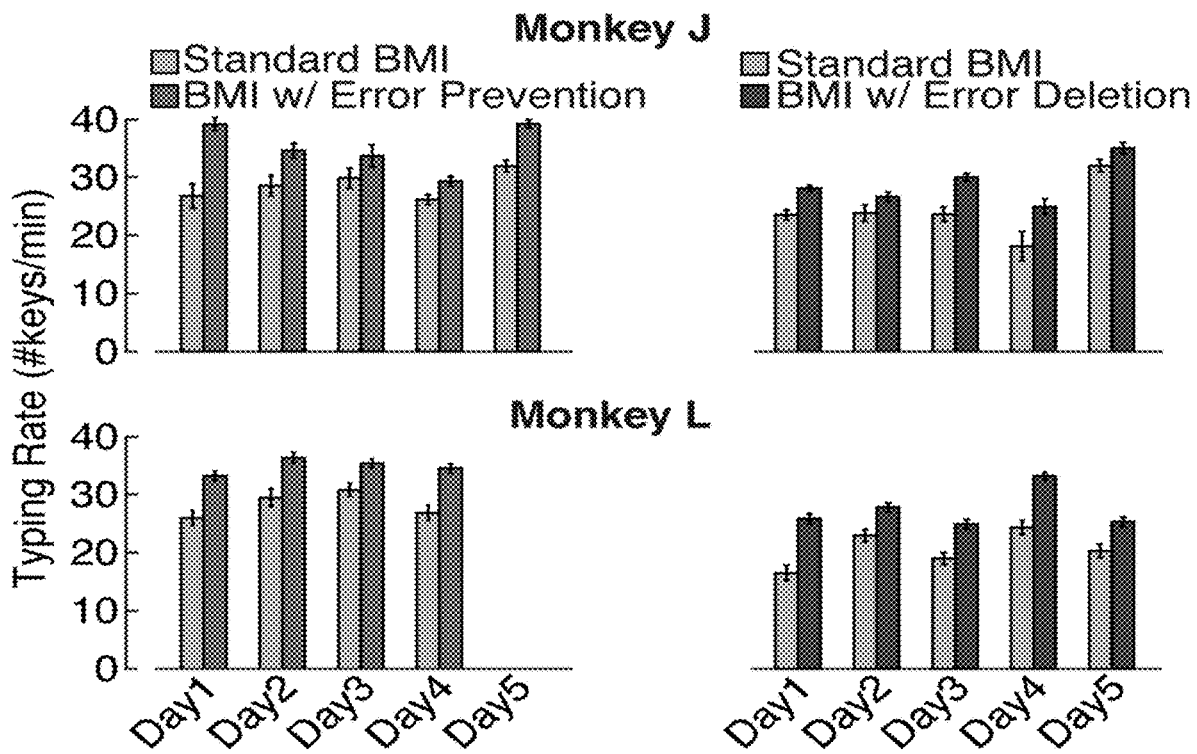

In a typing task, the user corrects his mistakes by selecting the 'delete' key. This manual corrective action is time-consuming. We predicted that an automatic error detector that can spare the user from manual correction would improve BMI performance. The ability to predict putative errors before target selection and to decode errors with high accuracy around 400 ms after target selection enabled us to implement two modes of error detection and mitigation for online BMI use. The first mode is error prevention (FIG. 3B, green), which estimates whether the upcoming target selection is erroneous based on the neural activity a few milliseconds before the end of the hold period. If so, the BMI system delays target selection by 50 ms (additional delays are also possible if the neural activity continues to signal task outcome error). This additional time gives the user an opportunity to move the cursor out of the presumably incorrect target's acquisition area, thus preventing errors from happening. The second mode is error deletion (FIG. 3B, purple), which detects errors after they occur (400 ms after target selection) and automatically "undoes" the presumably incorrect target selection; in a keyboard typing application, this would be the equivalent of deleting the preceding keystroke.

In online error detection experiments, we modified the task in two ways to make it more analogous to a human typing task. First, to simulate how users must press the 'delete key' after an incorrect selection and then correctly select the missed key, we cued a predefined 'delete' key after the incorrect selection and then cued the target that was initially missed. Second, we shortened the time between trials so that a new target was prompted 20 ms following target selection in error prevention and 420 ms in error detection experiments.

Figure 6:
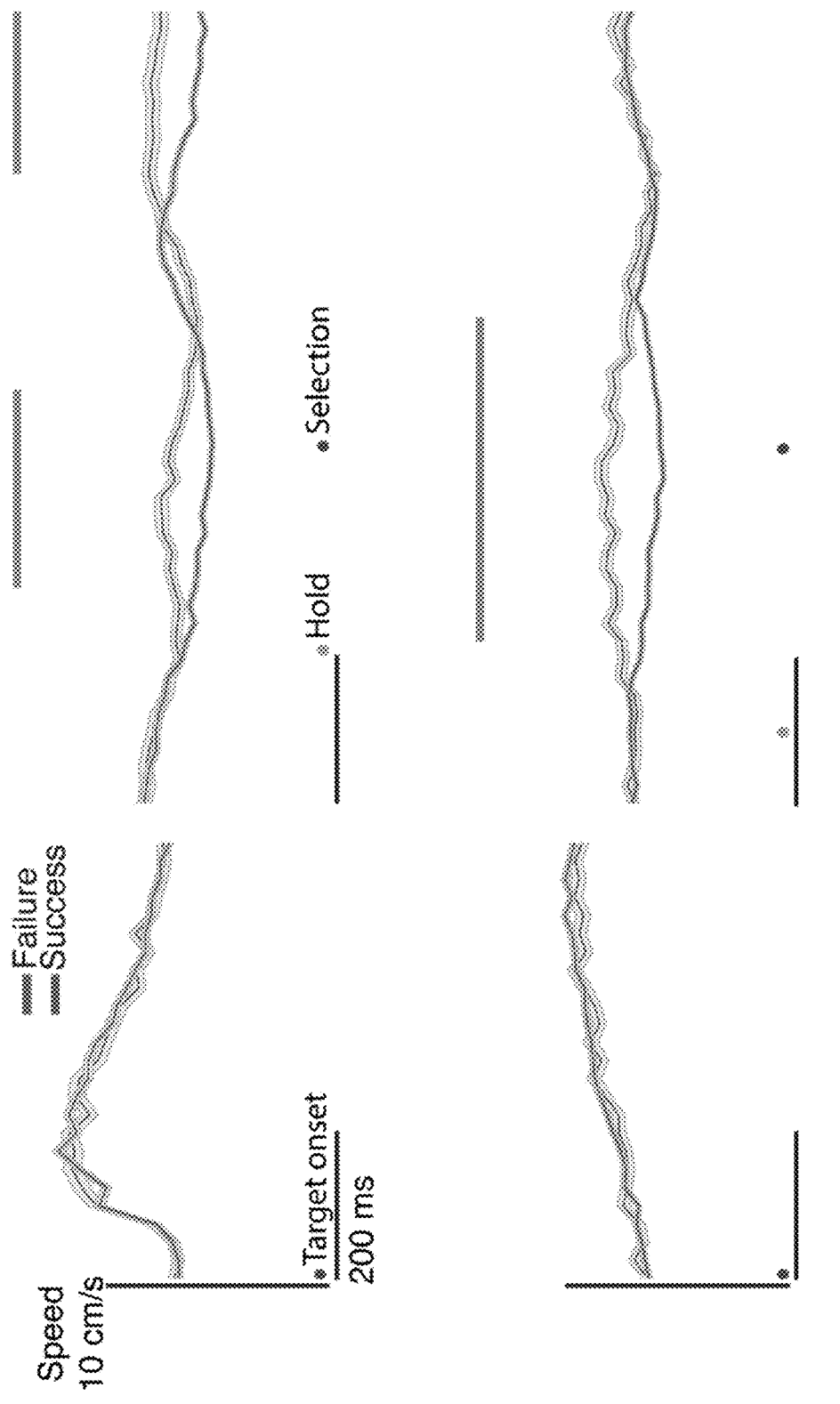
FIG. 6 shows according to an exemplary embodiment of the invention neural push speed profile (mean and SEM). Although there are neural push differences between success and fail trails, this is not the main reason for the high dimensional neural activity difference and the classification accuracy.

We implemented an error detector (FIG. 1A, i, red path) in parallel to a kinematic decoder for a real-time BMI task, and tested both the error prevention and error detection modes. The decoder was based on PCA (five leading principal components) and linear SVM (FIG. 6). Since we expected recordings to be quite stable from day to day, we pretrained the error detector on data collected on previous days. Each mode was compared separately to a standard BMI control without error detection in an A-B-A block format. We found that both modes improved the monkeys' typing rate across all days (t-test, p<0.01) by alleviating the need to correct mistakes (i.e., either by preventing errors or by auto-deleting them). Error prevention increased the average typing rate by 17% (J) and 33% (L). Error auto-deletion increased the average typing rate by 22% for both monkeys.

Controls for Kinematic Differences Between Successful and Failed Trials

Neural activity in motor cortex has many processes including, but not limited to, kinematics, kinetics, trial outcome (as reported here) and noise. Hence, the neural activity difference we observed between successful and failed trials may result from variables that indirectly correlate with trial outcome. If this is the case, these variables alone should be capable of distinguishing between successful and failed behavioral trials. Specifically, we asked if the difference in neural activity between trial outcomes, and the resulting high decoding accuracy achieved, could be a result of kinematic differences that are correlated with a trial's outcome. For example, what if the monkey consistently tried to correct his movement at the end of failed trials, but held still at the end of successful ones? More generally, the monkey may have had distinctly different movements after successful and failed trials. Indeed, we found that there were small differences between successful and failed trials' BMI-cursor kinematics (FIG. 6). The kinematic difference is presumably a result of kinematic-related neural activity driving the BMI-cursor through the decoder algorithm. We call this neural activity the 'neural push' because it reflects the neural activity's immediate influence on decoded velocity (see Methods: BMI Cursor Control). To ask whether these differences are a major contributor to the decoder's ability to predict task outcome, we conducted two comparisons (FIGS. 7A-B). To perform these comparisons we made use of a unique aspect of the BMI framework: we have full knowledge of how neural activity relates to movement, via the decoder algorithm of our design. In contrast, the relationship between neural activity and natural hand movements (e.g., kinematics, kinetics) is not entirely understood.

Our first analysis controlled for the effect of kinematics on decoding accuracy by regressing out kinematic information (cursor velocity) from the neural activity of each day (using least squares methods). We found that regressing out kinematics from the neural activity did not affect decoding performance (FIG. 7A; 'Neural'—J: 97±0.5, L: 94±0.5, 'Neural w/o Kin'—J: 97±0.4, L: 94±0.6; t-test, J: p=0.69, L: p=0.95). Our second analysis evaluated outcome decoding accuracy when decoding with kinematics and neural-push in different coordinate systems (Cartesian and Polar). We compared the performance of this decoder to decoding with neural activity alone ('Neural') and found that kinematic decoders (FIG. 7A, classification accuracy<77%) performed better than chance (t-test, p<1e−6) but much worse than decoders based on neural activity ('Neural'—J: 97±0.5, L: 94±0.5; t-test, p<1e−16). We also wanted to similarly verify that the signal before the target selection time is not primarily kinematics-related. To do, so we repeated these two analyses with data limited to before selection time (FIG. 7B). Regressing out kinematics from the neural activity in this case had small effect on the decoding performance ('Neural'—J: 83±1, L:J: 86±1 'Neural w/o Kin'—J: 85±1, L: 88±2; t-test, J: p<1e-3), but the kinematic decoders had significant lower performance than decoders based on neural activity (classification accuracy<75%, t-test p<1e-14). Based on these analyses, it appears that although there exist kinematic differences between successful and failed trials, this information alone does not account for our ability to decode trial outcome accurately. Thus, there is another source of neural information that discriminates between the two outcomes that enables an observer of the neural state to detect errors with high performance.

Controls for External Cue Differences Between Success and Failure Trials

The second concern that we addressed is whether the neural differences between successful and failed trials and our corresponding high decoding accuracy is a result of experimental elements that are different between successful and failed trials but are not directly related to the monkey's internal recognition/prediction of the trial's outcome. These three experimental elements are: 1) cued target color, which changes to blue preceding selection in successful trials, 2) auditory feedback, which is different for each outcome, and 3) liquid reward, which is given only in successful trials. To examine the influence of these elements on neural activity, we conducted online control experiments with monkey J, again using an A-B-A block format where A is the typical task and B is a modified task that omits the experimental factor in question.

Figure 8:
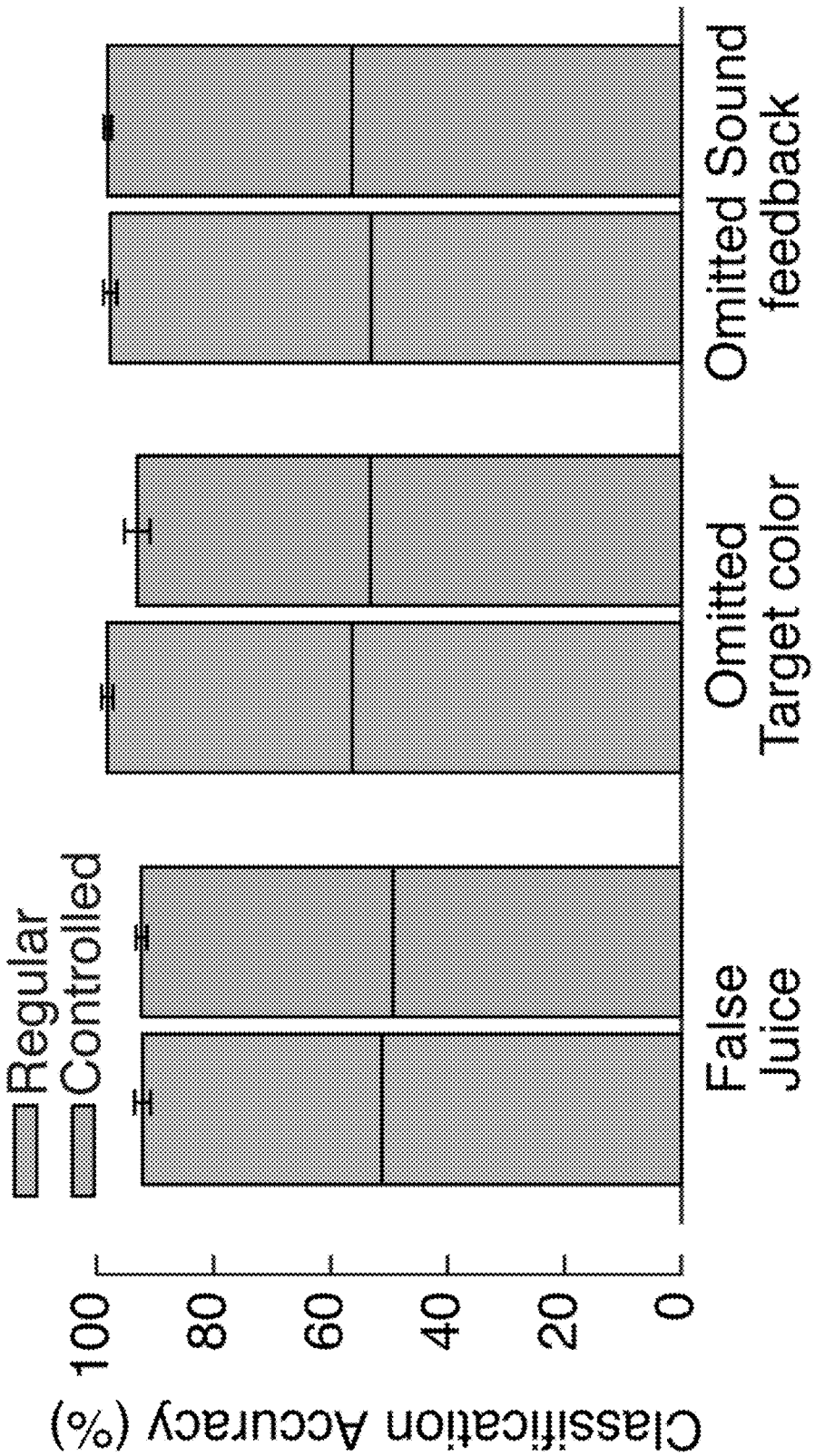
FIG. 8 shows according to an exemplary embodiment of the invention control experiments examining the influence of experimental cues on the decoded trial outcome. Single trial task outcome decoding accuracy during additional experiments designed to control for external cues about task outcome: false juice (juice was given after all trials), omitted target color (cued target color did not change to blue) or omitted sound (without sound feedback). Each condition was compared to interleaved blocks of the regular experiment setup. Removing any of these external cues did not have a substantial effect on decoding accuracy.

We examined 1) the effect of color by always keeping the cued target green, even while it was being held, 2) the effect of auditory feedback by turning off all auditory feedback, 3) and the effect of reward by rewarding the monkey on both successful and failed trials (FIG. 8). While reward and auditory feedback did not affect decoding performance (t-test, $p>0.3$), the color change had a minor effect (5% decoding accuracy difference, t-test $p<0.01$). A possible explanation for this performance difference is that the cued target color change when it is being held is a very salient aspect of the visual feedback to the monkey that he is selecting the correct target; its absence decreases the monkey's certainty that he is selecting the right target (e.g., he may think he is not holding the cued target even while he is doing so). Alternatively, the color, which has a movement-related meaning in this task, could be affecting motor cortical neural activity. Although, traditionally, M1 and PMd are not considered to be modulated by purely sensory input such as color and luminance if they are not correlated with movement. Nevertheless, our observation that without target color the classification accuracy is high (92%) indicates that another signal, unrelated to this color change, correlates with trial outcome in PMd/M1.

Together, these controls are consistent with the concept that the neural activity modulation we have described and decoded reflects a putative task outcome error signal that cannot be explained by kinematics or experimental cues alone.

Dissecting the Putative Outcome Error Signal

Thus far we have presented evidence supporting the existence of a difference in neural activity between successful and failed trials. However, single electrode analysis in the high dimensional neural space is limited in the way we can understand the latent processes that drive the measured neural activity. Filter out irrelevant processes will enable a clearer view of the outcome related neural activity. To better understand the putative error signal's temporal properties, whether it differs depending on the relative direction of the correct and (mis)selected target, and to further investigate its relation to movement-related neural activity, we employed dimensionality reduction methods to summarize and dissect the putative outcome error signal. Such techniques are often used to summarize properties of high-dimensional data (e.g., neural population activity) for visualization and inference. In dimensionality reduction technique we are interested in isolating the relevant information, which in our case is the difference between failed and successful trials (i.e., the error signal). Any two conditions (e.g., success and failure) can be represented with their average $Y_{cm}=(Y_s+Y_f)/2$ and difference $Y_{df}=Y_s-Y_f$; i.e., common and differential modes. Here, the common mode contains activity related to performing the task but unrelated to the specific outcome. To determine the error-related subspace and filter out common processes, we performed principal component analysis (PCA) on the differential mode; i.e., difference in the neural activity between the outcome-averaged successful and failed trials (see Methods infra: dimensionality reduction via PCA). In doing so, we constrain the dimensionality reduction to focus on the difference between outcomes.

First, to determine the putative outcome error signal dimensionality and dynamics we examine its principal components (PCs) and their explained variance (FIG. 9A-B). The three leading principal components (PCs) (named outcome-error subspace, $M^{OE}$) capture 88±1% (J) and 82±1% (L) of the variance of the averaged neural activity difference (FIG. 9A, red). Surprisingly, both monkeys' neural activities showed similar dynamics in these subspaces (FIG. 9B). This suggests that a major contributor to the putative outcome error signal is not related to a monkey-specific stereotypical movement or neural response pattern following successful versus failed trials, and may instead reflect a general feature of outcome error-related neural dynamics in these cortical areas.

Figure 10:
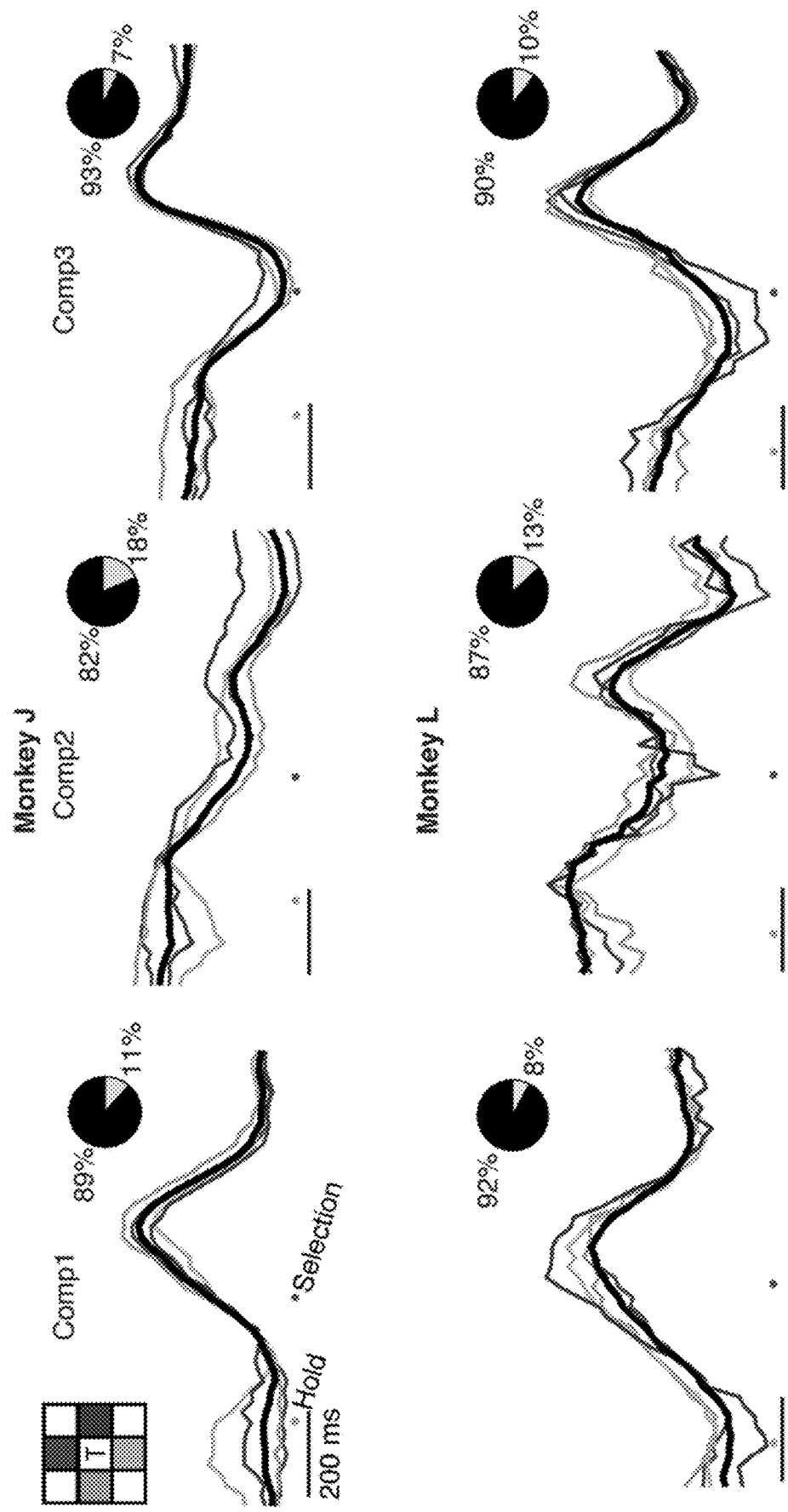
FIG. 10 shows according to an exemplary embodiment of the invention putative outcome error signal directional independency. Time course of the neural activity projected into the three leading components after alignment (as described in FIGS. 9A-B). Trials are now divided based on the relative direction between the incorrectly selected target and cued target location (see inset mapping, 'T' indicates the cued target) and black trace shows average across direction. Pie charts show what portion of the overall neural variance captured by each component is explained by the average error signal (black) versus the relative direction of the erroneously selected target (yellow).

Next, we explored the putative outcome error signal direction sensitivity. We would expect an outcome error signal to be direction independent, in contrast to execution error signal, which suppose to provide directional information about the error. To do so, we projected the neural differences between the average of successful trials and the trial averages for four failed directions into outcome-error subspace (FIG. 10). We found that the putative error signal is largely direction-independent. Consistent with a common and differential mode, the total variance of the four projections can be divided into two components: variance that is related to the common activity across the four directions of error (i.e., the average across directions) and one that is related to the activity that is different between them. We found that 90% (J) and 91% (L) of the variance of the three leading PCs is explained by the common error neural activity across directions and the rest by the difference in activity across directions (FIG. 10).

Lastly, defining the signal subspace enable us to investigate the relationship between the putative outcome error signal and kinematics in a different approach than we presented herein. We asked how much of the putative outcome error signal variance can be explained by ongoing movement, i.e., how much of the variance is projected to movement-related versus movement-null neural subspace. As before, the BMI framework enables us to determine the mapping from neural activity to movement (see Methods infra: BCI cursor control). This mapping is a linear projection of the neural activity to velocity in the x- and y-direction. The mapping matrix $M_2 \in R^{2 \times \#Electrodes}$ defines two complementary and orthogonal neural subspaces: one where neural activity affects cursor movement ($M^{Po} \in R^2$, decoder-potent space) and another that where the neural activity does not affect cursor movement ($M^{Null}=Null(M^{Po})$, decoder-null space). We call these subspaces the decoder-potent and decoder-null space, respectively and are closely related to output-potent and output-null subspaces. Using this approach, we found that less than 1% of the putative outcome error signal variance is explained by the 2D movement-related neural activity ($M^{Po}$, 2D decoder-potent space) compared to 85% on average explained by the three leading PCs of the outcome-error subspace. Moreover, 99% of the difference in neural activity is confined to the decoder-null space. This means that the outcome-error subspace ($M^{OE}$) is nearly orthogonal to the decoder-potent space ($M^{Po}$), which strengthens our confidence that the putative outcome error signal is not directly related to movement intentions.

Directional Error Detection

Figure 11:
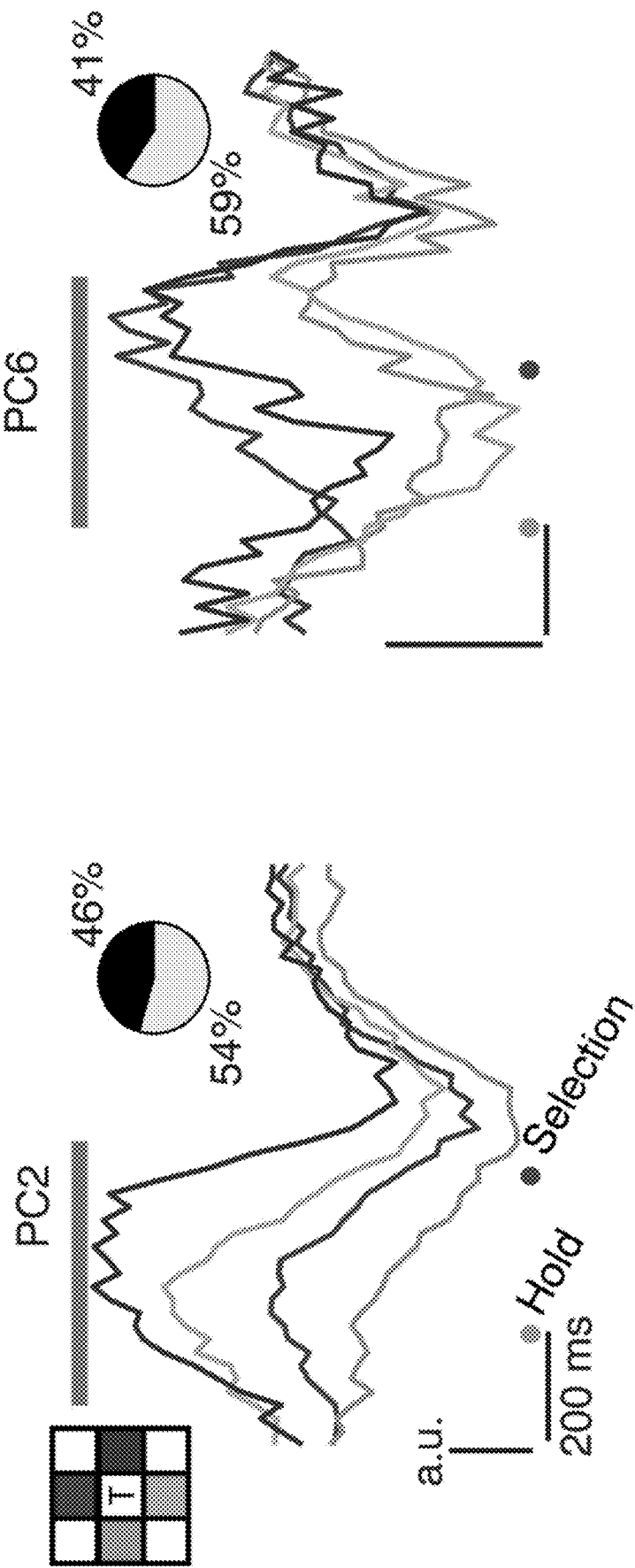
FIG. 11 shows according to an exemplary embodiment of the invention directional error signal (see FIG. 9A-B for monkey J) Monkey L's neural activity is projected into the two PCs which have a high (above 50%) directional variance. These PCs capture 22% and 17% of the total neural variance, respectively. Pie charts show the variance source distribution between the variance resulted from the average error signal ('black') and the direction of the error ('yellow').

Despite finding that most of the putative outcome error signal was directionally independent, we investigated whether we could nonetheless also find a different signal that correlates with the direction of the error in the motor cortex. To find a different subspace that captures variance related to the directions between the cued and incorrectly selected target, we performed additional PCA on the neural differences between the average of successful trials and the trial averages for four failed directions (concatenated in time, see Methods infra: Dimensionality reduction). This technique is similar to our method described herein to find the putative outcome error subspace, except here we focus on observing the variance that distinguishes between which direction pointed towards the correct target. We found that there exist some neural dimensions whose variance is mostly explained by the differences between direction conditions rather than by the condition average signal (FIG. 4A—yellow part in the pie chart, see FIG. 11). This relationship between sources of variance is opposite to the putative outcome error subspace found previously (FIG. 9A-B), where most of its variance was direction independent. We found that 4% (J) and 5% (L) of the two directional PCs variance is explained by movement-related neural activity ($M^{Po}$, 2D decoder-potent space). In contrast, less than 1% of the variance of the two directional PCs can be explained by the outcome-error subspace ($M^{OE}$). These indicating that some of the directional-error signal can be explained by kinematics (i.e., the monkey trying to move the cursor to the correct target) but none it cannot be explained by the putative outcome error signal. These results are consistent with the Inoue and colleagues findings, which showed that direction error correlates exist in the motor cortex.

This surprising activity variation across directions (FIG. 4A) led us to do an offline analysis to evaluate if one could decode error direction (i.e. where the cued correct target lay with respect to the incorrectly selected target) on single trials. As proof of concept for future BMI development, we compared the error direction classification accuracy (using the six leading PCs) of four potential directions (FIG. 4A) with random data (random permutation of the error direction) using a nearest-neighbor classifier. We found that we were able to decode better than chance in both monkeys (FIG. 4B; J: 68±1%, L: 76±2%; t-test, p<1e−10). Decoding accuracy can be improved in future work by better characterizing the directional sensitive subspace, projecting to more PCs and by using more advanced classification methods. Correctly decoding the direction of the error would result potentially even higher BMI performance by selecting the intended key.

Conclusion

The neural engineering contribution of this invention is that we designed and implemented in closed loop an intracortical BMI decoder that utilized biological error signal to improve performance, while current BMIs decode only neural correlates of movement intention. We demonstrated an error decoder with two that improved the BMI performance in closed-loop, real-time experiments. The two modes are different in their error decoding latency (i.e., how long we wait after selection before we decode) and the corrective action (prolonging target-hold time vs. deleting the last key). On the one hand, increasing the decoding latency increases its accuracy (FIG. 2D) and thus the typing rate, but on the other hand, it prolongs the trial length, which decreases typing rate. While we choose in the present study what we felt was a reasonable decoding latency and showed that it worked well, we note that this tradeoff can be optimized offline and adapt online.

Our error detection (prevention and auto-deletion) techniques could be applied to a broad range of BMI tasks to intervene with corrective actions. In a computer cursor control task, it can be used to prevent incorrect clicks during typing. During control of a robotic arm, task outcome error detection can likely be used to cancel the last command (e.g., grasping) and return to a previous state (e.g., the state of the robotic arm a second ago). In addition, error signals can also be used to update the decoder parameters and prevent future errors. While execution error can be used to update decoder parameters themselves, outcome error can be used to adjust the learning rate of an adaptive algorithm, by, for example, increasing the learning rate after errors.

Implementing a similar error detection strategy in a clinical human BMI should be straightforward as long as this signal appears in the motor cortex. However, we predict that an at least one difference will be encountered compared to this pre-clinical monkey study that can improve error detection performance. When a human user performs BMI typing, we expect that there will be a natural delay between selecting a key and the initiation of movement towards the next key, due to cognitive processes related to choosing the next letter. In contrast, in our work, the target sequence was determined by the experimenter and not chosen by the monkey. Therefore, the delay between the time of selection and the initiation of a movement to the next target was only dependent on the visual stimulus processing latency. Hence, in a human BMI setting, it may be possible to extend the latency of error detection, which would improve the outcome decoder without increasing the average trial length.

Figure 4A:
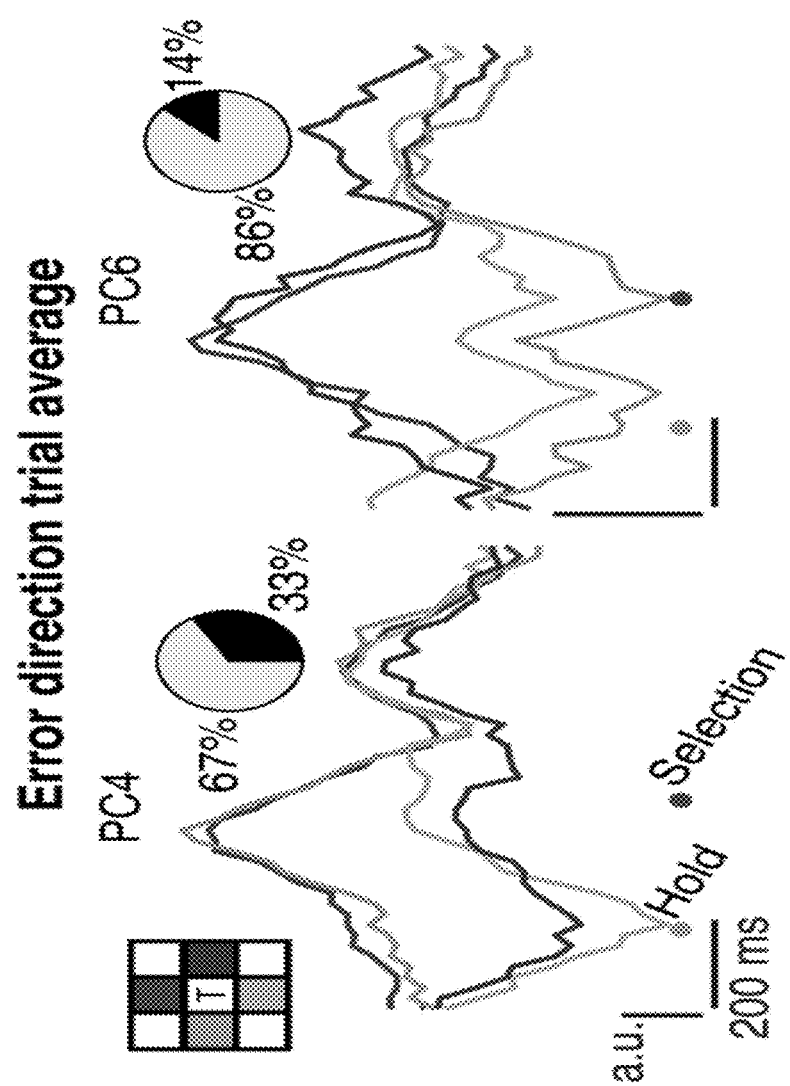
FIGS. 4A-B show according to an exemplary embodiment of the invention information about the error direction is present in the neural signal and can be decoded.
Figure 4B:
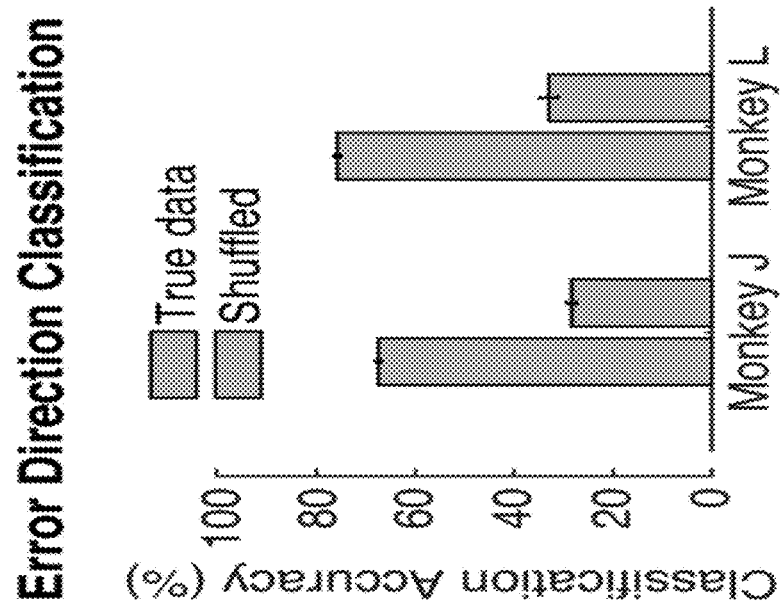

Finally, we also showed the ability to detect the direction of the incorrectly selected target relative to the correct target (FIGS. 4A-B). Detecting the direction of task-outcome error—rather than just its occurrence—in a real-time BMI could be used to intervene with even more helpful corrective actions. For instance, the system could automatically select the decoder's estimate of what the intended key was (during typing), or move the prosthesis towards the intended object (during robotic arm use). Knowledge about the error direction could also be utilized to perform supervised update decoder parameter updates.

Methods

Behavioral Tasks

All procedures and experiments were approved by the Stanford University Institutional Animal Care and Use Committee. A rhesus macaques (monkeys J and L) were trained to perform point-to-point virtual cursor movements in a 2D plane using either hand movements or BMI control. They were free to move their arm even during BMI control. A keyboard-like task was modeled. The goal of the task and the experiment timeline depicted in Results-Task section and in FIGS. 1A-D. The workspace was 40×32 cm and had in its center a 24×24 cm grid uniformly divided into n×n (n=6-8) contiguous, non-overlapping square target acquisition regions (24/n cm). Each target acquisition area contained, at its center, a circular visual representation of the target.

Neural Recording and Signal Processing

Monkeys J and L were implanted with two or one 96-electrode Utah arrays (Blackrock Microsystems, Inc.), respectively, using standard neurosurgical techniques 63-72 and 83-91 months prior to this study. J's arrays were implanted into the left cortical hemisphere; one array went into the primary motor cortex (M1) and the other into the dorsal premotor cortex (PMd), as estimated visually from local anatomical landmarks (FIG. 1B). L's array was implanted into the right hemisphere boundary between motor cortex and premotor cortex, as estimated visually from local anatomical landmarks (FIG. 1B). Since L had only one array, anterior electrodes were labeled as 'Pmd' and posterior electrode labeled as 'M1' in our analysis (gray areas in FIG. 1B).

Voltage signals from each of the electrodes were bandpass filtered from 250 to 7500 Hz. A spike was then detected whenever the voltage crossed below a threshold set at the beginning of each day (at −4.5× rms voltage). Contralateral hand position (for decoder training) was measured with an infrared reflective bead tracking system (Polaris, Northern Digital) polling at 60 Hz.

BMI Cursor Control

At the start of each experiment, we collected a training dataset of 500 arm-controlled trials of a planar random target reaching task. This data were used to train a Feedback Intention Trained Kalman filter (FIT-KF) decoder, which operates at every time step on the observed firing rate vector $y_t \in R^N$ (N=192 for J and 96 for L). The decoder outputs a velocity command every 25 ms from input consisting of binned spikes counts from the previous 25 ms. Briefly, FIT-KF is a streamlined version of the ReFIT-KF (see e.g. U.S. Pat. No. 8,792,976) and improves upon a standard KF by adjusting kinematics of the training data to better match the subject's presumed movement intention. Note that for some days of the experiment we did not zero training set velocities during the hold epoch. We have used a suboptimal decoder to reduce the performance of the monkeys and achieve higher error rate to improve the statistical power.

The velocity Kalman filter (VKF) converges quickly to a steady state:

$$v_t = M_1 v_{t-1} + M_2 y_t \quad (1)$$

where $v_t \in R^2$ is the velocity of the cursor. We call the first term ($M_1 v_{t-1}$) the momentum (a state dynamic matrix that smooths the velocity) and the second term ($M_2 y_t$) the 'neural push' (a neural activity mapping to velocity). The linear mapping $M_2$ defines a decoder-potent space, neural activity in that subspace will affect the kinematics. However, neural activity outside this subspace, i.e. in the decoder-null space, will have no direct effect on kinematics. The steady state equation can be also written as:

$$v_t = \Sigma_{\tau=0}^{t} M_1^{t-\tau} \cdot M_2 y_\tau \quad (2)$$

which show that the current course velocity is a causal smoothing of the neural push.

Offline Analysis

For all offline analyses, multiunit threshold crossing spike counts from each electrode were binned every 25 ms ($y_k \in R^N$) and each trial ($Y_i \in R^{N \times K}$, where K is the number of time bins in the trial) was aligned to target selection time (t=0, FIG. 1A). For statistical significance, we used two-sampled t-test with confidence level of α=0.05 (unless stated otherwise) and Bonferroni correction (to account for the familywise error rate).

Percentage of Significant Electrodes

To smooth the results, an electrode considered as significant for the population analysis, if it crossed the confidence levels in two consecutive time samples. The population significance percentage at each time sample is the average across days of significant electrodes' percentage. The average, standard error (SE) and latency of the population significance percentage were computed using bootstrap (with 500 samples). For PMd and M1 comparison, we used the same technique while limiting the computation to the relevant electrodes as shown in FIG. 1B.

Dimensionality Reduction Via Principal Component Analysis (PCA)

We conducted principal component analysis (PCA) on the neural activity difference between the successful and failed trial-average:

$$\Delta y_k^\mu = \frac{1}{N_s} \sum_{i \in Suc} y_k^i - \frac{1}{N_f} \sum_{i \in Fail} y_k^i, \Delta y_k^\mu \in R^N \quad (3)$$

This was to focus on the variance between outcomes (successes and failures) rather than overall variance (which includes other signals). Filtering out non informative signals and reduce the dimensionality of the data (and number of classifier's parameters) increase the decoding accuracy (see classification via support vector machine).

From the same reason, we use a similar technique to find the subspace that captures the directional error signal (FIGS. 4A-B). We conduct PCA on the concatenated (in time) differences between success trial-average and four failed directional trial-average.

Classification Via Support Vector Machine

For all our classification, we used a linear support vector machine (SVM) to classify trials between successful and failed categories. The data were composed of labeled (successful or failed) trials $Z_i \in R^{L \times K}$, where L is the number of number of electrodes or principal components or kinematic component and K is the number of time bins in the chosen time window. Each example has L×K features and is labeled as successful or failed. Given a set of examples, the SVM training algorithm builds a model that can be then used to assign new examples into one of these two categories. In the case of principal components (PCs) classification, we found that five PCs is optimal for SVM. We note that for each delay period (FIG. 2D and FIGS. 3A-B) we needed to build a separate classifier, which has different number of features (number of time bins).

For offline classification we used 10-fold cross-validation to estimate the classification accuracy and its standard error. To compute naive classifier (as control), we repeated the 10-fold cross validation when the labels of the trials (successful or failed) were randomly shuffled across the trials. Moreover, to assess the classifier bias towards one category (e.g., decoding 'successful trial' all the time), we compute the detection rate of successful and failed trials separately (e.i., true positive and true negative). When PCs were classified, to prevent the test set effect the PCs subspace, we conducted PCA on each training set of the cross-validation before classifying.

Online Error Detector

The online error detector was composed of two phases: dimensionality reduction (projection to PCs subspace) and classification (using SVM). Since the outcome decoding performance converges after approximately 2000 training trials, we trained the error detector on data set from previous days (6 days for J and 4 days for L).

Note

The main parameter in our error detector is the delayed time before decoding, i.e., how long after selection we should wait before decoding the outcome. On the one hand, increasing the decoding latency increases accuracy (FIG. 2D) and thus the typing rate, but on the other hand, it prolongs the trials length and decrease typing rate.

The typing rate is dependent on several parameters: the success rate of the user in the task (SR), the average trial length (T) and the cost of making an error (i.e. the additional trial necessary to select the delete key). The typing rate using a regular BMI without an error detector can be estimated offline by:

$$TR_{reg} = \frac{N_{char}}{\text{Total time}}$$
$$= \frac{N_{all} - 2 \cdot N_{Failed}}{N_{all} \cdot T}$$
$$= \frac{2 \cdot SR - 1}{T}$$

The typing rate using an error detector can be estimated offline using additional two parameters:
delay time ($t_{delay}$) and its corresponding detection accuracy (DA):

$$TR_{ED} = \frac{N_{char}}{\text{Total time}}$$
$$= \frac{N_{all} - 2N_{Failed} \cdot (1 - DA) - N_{Suc} \cdot (1 - DA)}{N_{all} \cdot (\overline{T} + t_{delay})}$$
$$= \frac{1 - (1 - DA)(2 - SR))}{\overline{T} + t_{delay}}$$

Since detection accuracy (DA) is an unknown function of the delay time ($t_{delay}$), we can find the optimal delay time empirically and adapt it online to maximize typing rate.

Some parts of the embodiments of the invention can be realized as computer-implemented code executable by a computer or realized as electronic chips which together with the electrical activity obtained from a subject through electrodes will be able to control via the brain machine interface a subject's limb, orthotics or prosthetics.

What is claimed is:

1. A brain-machine interface, comprising:
   at least one microelectrode array configured to be implanted into a subject's brain in the motor cortex region;
   a virtual keyboard comprising a virtual cursor; and
   a computing component, comprising:
      an intention decoder for decoding the subject's intention from a first neural signal; and
      an error signal decoder for decoding error signals from a second neural signal;
   where the intention decoder is directed to:
      obtain the first neural signal comprising at least one intracortical spike signal from the at least one microelectrode array describing neural activity representative of an intended action by the subject;
      infer the intended action from the first neural signal; and
      initiate the performance of the intended action using the virtual keyboard; and
   where the error signal decoder is directed to:
      obtain the second neural signal comprising at least one intracortical spike signal from the at least one microelectrode array describing neural activity in the subject's brain;
      reduce the dimensionality of the second neural signal;
      classify the second neural signal as an error signal based on the reduced second neural signal;
      delay selection of a key in the virtual keyboard when the error signal decoder detects an error signal; and
      cancel the performance of the intended action by the virtual keyboard.

2. The brain-machine interface of claim 1, wherein the at least one microelectrode array comprises a first microelectrode array and a second microelectrode array;
   wherein the first neural signal is obtained from the first microelectrode array; and
   wherein the second neural signal is obtained from the second microelectrode array.

3. The brain-machine interface of claim 1, wherein the dimensionality of the second neural signal is reduced using a principal component analysis; and the second neural signal is classified using a linear support vector machine.

4. The brain-machine interface of claim 1, wherein the cancelled action is to select a key in the virtual keyboard.

5. The brain-machine interface of claim 1, wherein the intention decoder is updated based on the classifications made by the error signal decoder.

6. A method for utilizing error signals to increase accuracy in a brain-machine interface system, comprising:
   obtaining a first neural signal comprising at least one intracortical spike signal from at least one microelectrode array in the motor cortex of a subject's brain describing neural activity representative of an intended action by the subject using an intention decoder;
   inferring the intended action from the first neural signal using the intention decoder;
   initiating the performance of the intended action using a virtual keyboard using the intention decoder, the virtual keyboard comprising a virtual cursor; and
   obtaining a second neural signal comprising at least one intracortical spike signal from the at least one microelectrode array describing neural activity in the subject's brain activity using an error signal decoder;
   reducing the dimensionality of the second neural signal using the error signal decoder;
   classifying the second neural signal as an error signal based on the reduced second neural signal using the error signal decoder;
   delaying selection of a key in the virtual keyboard when the error signal decoder detects an error signal and
   cancelling the performance of the intended action by the virtual keyboard using the error signal decoder.

7. The method for utilizing error signals to increase accuracy in a brain-machine interface system of claim 6, wherein at least one microelectrode array of the at least one microelectrode array is implanted into the subject's brain at the primary motor cortex region.

8. The method for utilizing error signals to increase accuracy in a brain-machine interface system of claim 6, wherein the at least one microelectrode array comprises a first microelectrode array and a second microelectrode array;
   wherein the first neural signal is obtained from the first microelectrode array; and
   wherein the second neural signal is obtained from the second microelectrode array.

9. The method for utilizing error signals to increase accuracy in a brain-machine interface system of claim 6, wherein reducing the dimensionality of the second neural signal comprises using a principal component analysis; and classifying the second neural signal comprises using a linear support vector machine.

10. The method for utilizing error signals to increase accuracy in a brain-machine interface system of claim 6, wherein the cancelled action is to select a key in the virtual keyboard.

11. The method for utilizing error signals to increase accuracy in a brain-machine interface system of claim 6, further comprising updating the intention decoder based on the classifications made by the error signal decoder.

* * * * *